United States Patent
Jackson

(10) Patent No.: US 10,894,108 B2
(45) Date of Patent: Jan. 19, 2021

(54) ANTIMICROBIAL FLOOR MAT

(71) Applicant: Douglas Jackson, Atlanta, GA (US)

(72) Inventor: Douglas Jackson, Atlanta, GA (US)

( * ) Notice: Subject to any disclaimer, the term of this patent is extended or adjusted under 35 U.S.C. 154(b) by 607 days.

(21) Appl. No.: 15/340,829

(22) Filed: Nov. 1, 2016

(65) Prior Publication Data

US 2017/0128606 A1 May 11, 2017

Related U.S. Application Data

(60) Provisional application No. 62/285,907, filed on Nov. 11, 2015.

(51) Int. Cl.
*A61L 2/22* (2006.01)
*A61L 2/24* (2006.01)
*A47L 23/26* (2006.01)

(52) U.S. Cl.
CPC .............. *A61L 2/22* (2013.01); *A47L 23/266* (2013.01); *A61L 2/24* (2013.01); *A61L 2202/14* (2013.01); *A61L 2202/15* (2013.01)

(58) Field of Classification Search
CPC .......... A61L 2/22; A61L 2/24; A61L 2202/14; A61L 2202/15; A47L 23/266
See application file for complete search history.

(56) References Cited

U.S. PATENT DOCUMENTS

| | | | | |
|---|---|---|---|---|
| 5,991,967 A * | 11/1999 | Williams | ............... | A47L 23/263 15/311 |
| 6,021,792 A * | 2/2000 | Petter | ..................... | B08B 3/026 134/104.2 |
| 6,125,482 A * | 10/2000 | Foster | ..................... | E03C 1/046 4/623 |
| 6,651,589 B2 * | 11/2003 | Greeson | ............... | A01K 13/003 119/656 |
| 6,668,842 B1 * | 12/2003 | Wilke | ..................... | A47L 23/02 134/113 |
| 9,107,973 B1 * | 8/2015 | Robinson | .................. | A61L 2/22 |
| 2004/0091389 A1 * | 5/2004 | Malkin | .................. | A61B 1/123 422/26 |
| 2006/0048469 A1 * | 3/2006 | MacLean | ............. | A01K 1/0103 52/220.3 |
| 2008/0104782 A1 * | 5/2008 | Hughes | .................. | A47L 23/02 15/30 |
| 2010/0008819 A1 * | 1/2010 | Hyde | .................... | E05B 1/0069 422/3 |
| 2010/0303671 A1 * | 12/2010 | Bertrand | ................. | A61L 2/202 422/29 |
| 2012/0167325 A1 * | 7/2012 | Omidi | .................... | A47L 23/263 15/210.1 |
| 2013/0213443 A1 * | 8/2013 | Garcia | ...................... | A61L 2/07 134/99.2 |

* cited by examiner

*Primary Examiner* — Regina M Yoo
(74) *Attorney, Agent, or Firm* — Polsinelli PC; Elton F. Dean, III

(57) ABSTRACT

Disclosed herein are devices, designs, and methods of using a device for sanitizing feet, shoes, or other surfaces in contact with the floor. The apparatus is capable of detecting the presence of a user and automatically spraying the feet of a user with a sanitizing fluid. Fluid is expelled through an elevated grate, which allows the user to stand on an elevated grate and have their feet sanitized without exposing their feet to a dirty pool of liquid.

17 Claims, 40 Drawing Sheets

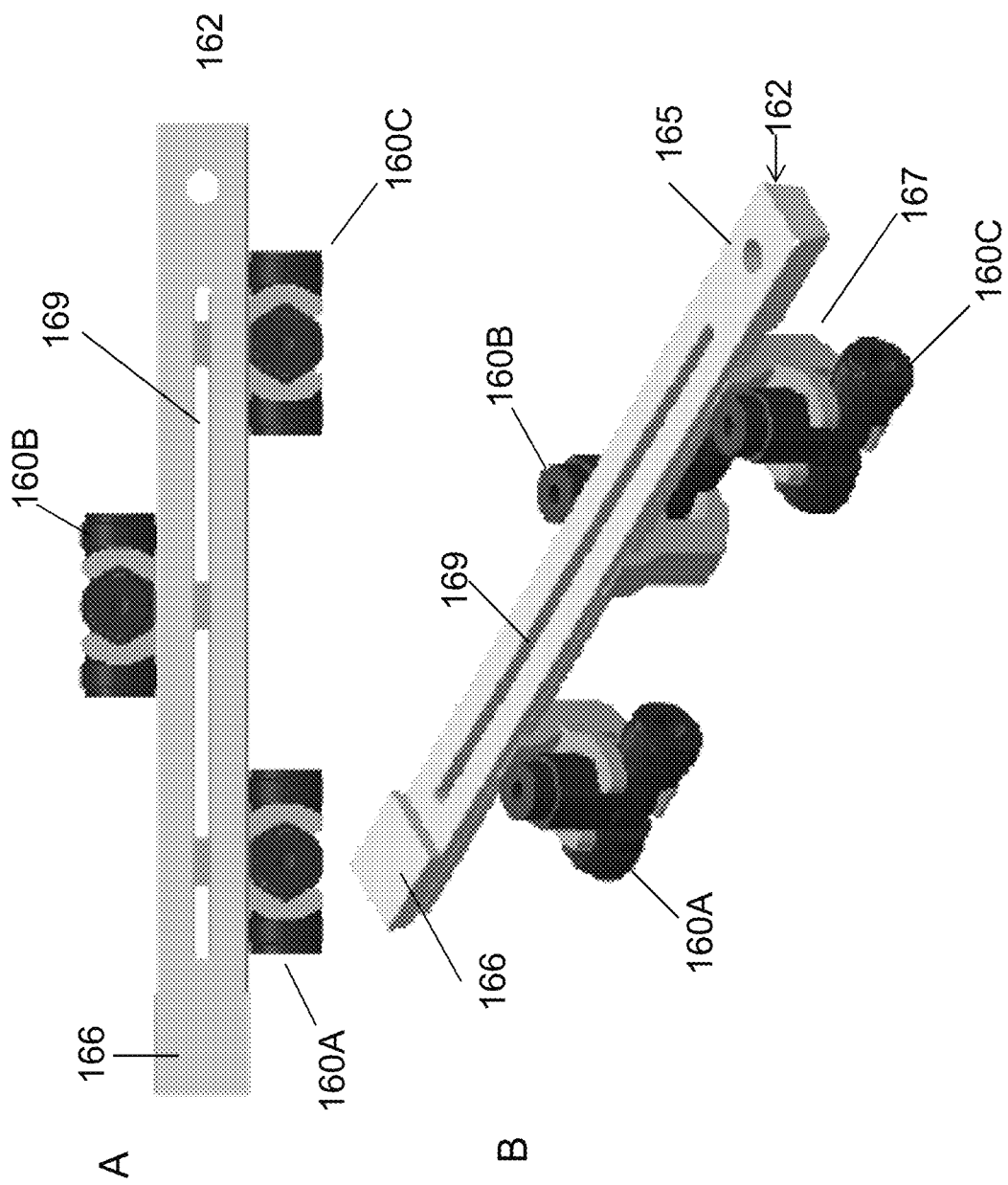

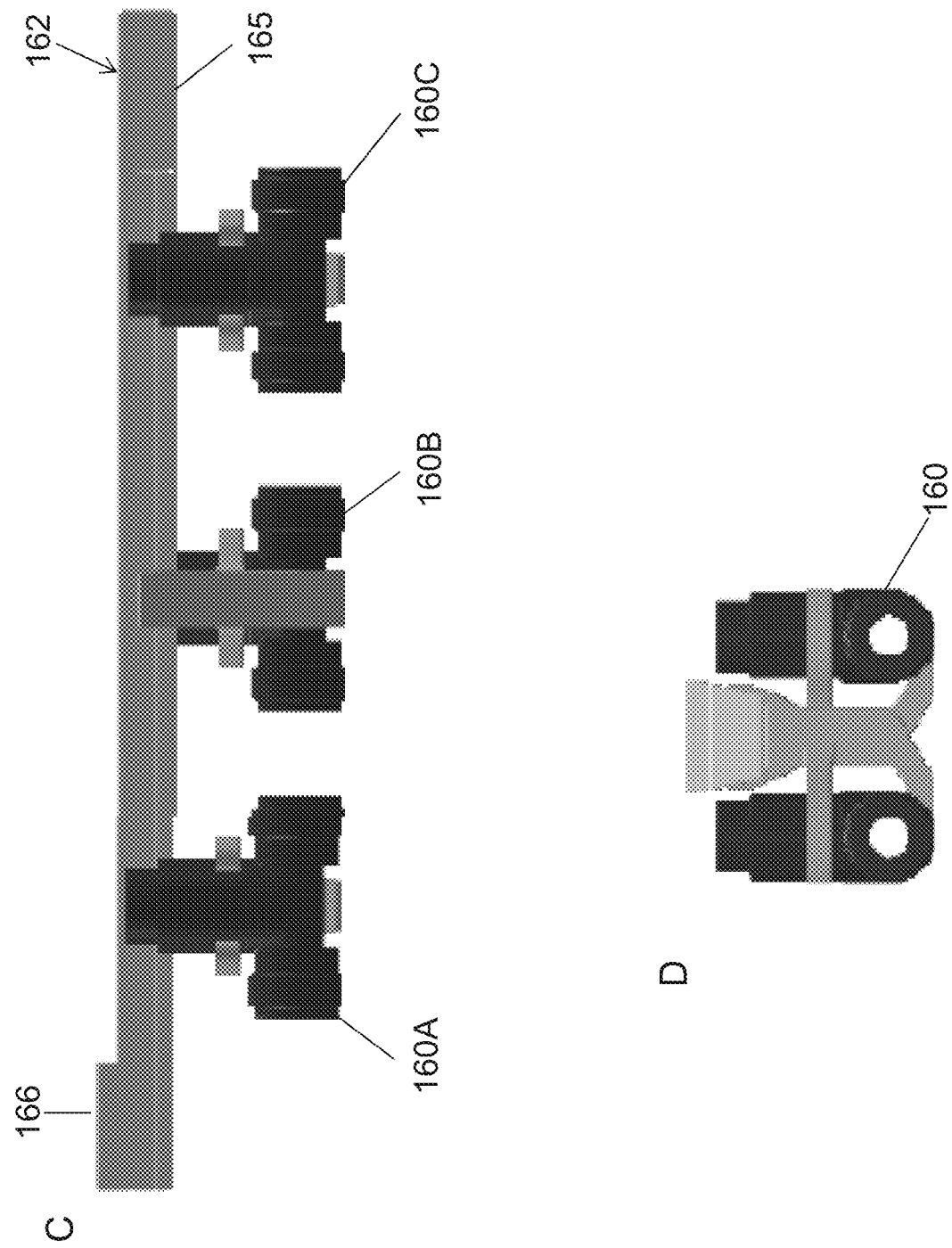

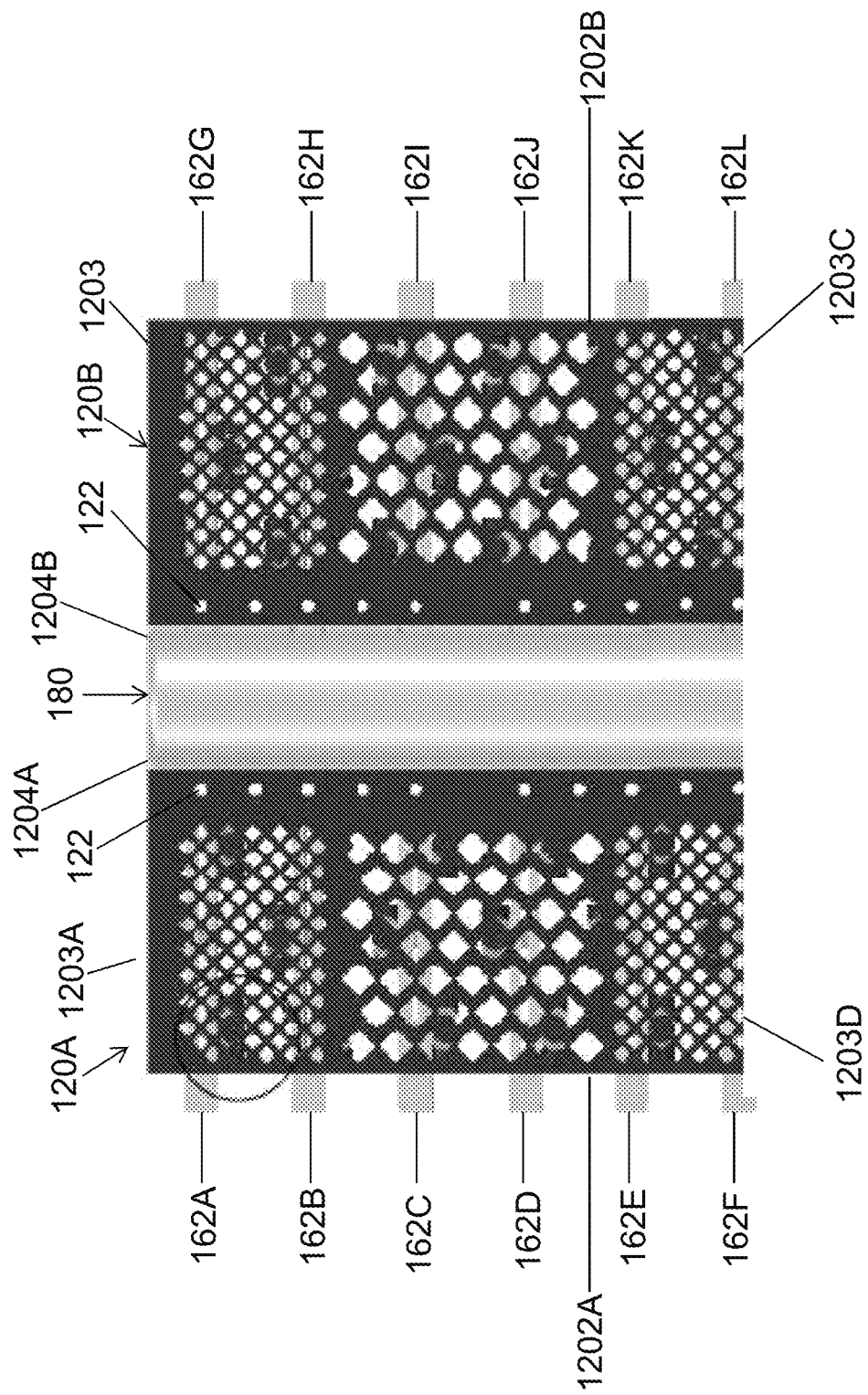

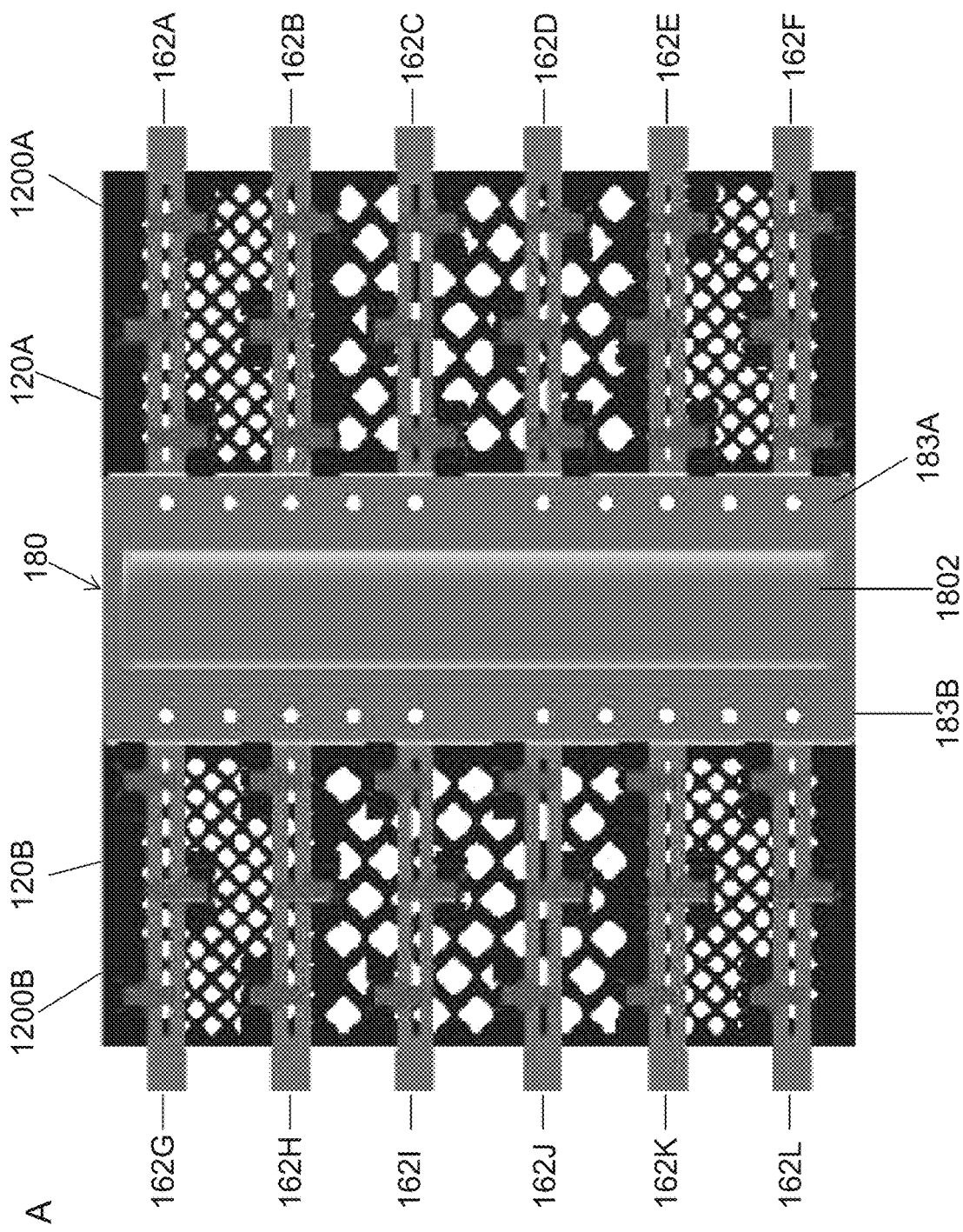

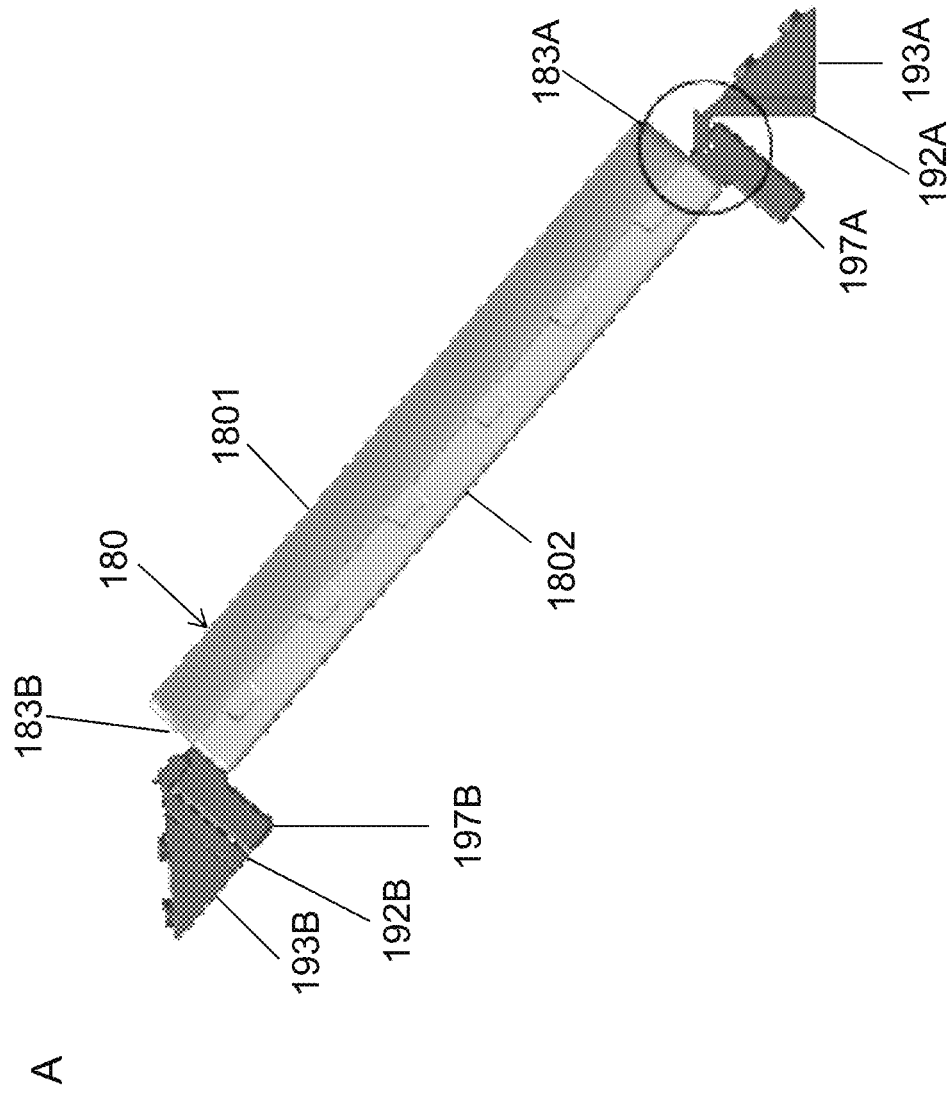

B

ANTIMICROBIAL FLOOR MAT

RELATED APPLICATIONS

This application relates to and claims priority to U.S. Provisional Patent Application No. 62/285,907, which was filed Nov. 11, 2015 and is incorporated herein by reference in its entirety.

BACKGROUND OF THE INVENTION

Harmful microbes are generally unwanted in places such as hospitals, greenhouses, infant daycares, and concentrated animal feeding operations. These microbes may cause disease or even kill. In a medical setting, such as an intensive care unit, immunocompromised patients may be negatively impacted by unwanted pathogens that often enter the room on a visitor's shoes.

Daycares are also concerned with unwanted pathogens entering the facility because infants do not have fully developed immune systems until they are around six months old. But, infants are often cared for in daycares where they are allowed to crawl on the floor. Infants put items such as bottles, toys, and pacifiers in their mouths even if these items have been in contact with the floor. Infants also put their hands in their mouths. Because infants lack fully developed immune systems, unwanted pathogens on the daycare floor may make infants sick. It is difficult to keep the floors free from outside debris and pathogens because parents, visitors, and teachers enter and leave the room many times a day.

The food industry also must address unwanted pathogens in processing facilities. Animals such as pigs, chickens, turkeys, and cows are often raised in controlled environments. Animals raised in these concentrated animal feeding operations may not have fully developed immune systems. Disease in these animals may have detrimental consequences. Farmers, visitors, and other workers must enter these concentrated animal feeding operations to feed animals, maintain equipment, and take care of animals. People who enter concentrated animal feeding facilities may unknowingly bring in unwanted pathogens on their feet, potentially exposing livestock to harmful or deadly disease. This type of contamination is also a problem to be solved in greenhouses and food processing facilities.

Booties or other foot coverings are often used for keeping contaminants out of medical settings and infant day cares. But, these booties require a user to have their hands free for placing the booties on their feet. Additionally, bootie placement takes time. Furthermore, booties must be washed or disposed after use.

Traditional disinfectant mats have been used in concentrated animal feeding operations, food processing facilities, and greenhouses to keep these facilities free of unwanted pathogens. These traditional mats require a time consuming process for setting up a pool of disinfectant for users to stand in. First a sanitizing liquid is mixed and poured into a pool. Then the mat is carefully placed over the pool, avoiding splashing or contacting the skin with the liquid. Next, additional sanitizing fluid is poured over the mat, readying the traditional mat for a user to stand atop the mat. While standing on the mat, users move their feet back and forth to remove debris and disinfect their feet.

The same pool of disinfectant is used for each user. This reuse of disinfectant may degrade the efficacy of the solution. After several uses, the traditional disinfectant mat becomes grimy and full of debris that must be cleaned. Because a used mat has an open pool of dirty contaminated liquid, the pool is difficult to move without spilling or splashing the contaminated liquid.

Cleaning these traditional mats, usually by hand, is a time consuming and dirty process that takes several steps. First, the dirty mat must be removed from the pool of contaminated liquid. Then, the pool of dirty liquid must be disposed and the pool must be cleaned. Next, the mat must be cleaned using running water. Then, the wet mat must be dried. While the mat is drying, another mat may be used in the pool, or the user must wait until the cleaned mat is dry.

What is needed is a hands-free device that a user can stand on and have their feet sanitized without exposing their feet to a dirty pool of liquid. The device should be easy and fast to use by anyone who enters a facility, regardless of training. Cleaning the mat should also be easy and fast.

SUMMARY OF THE INVENTION

The present application relates to a sanitizing mat for the sanitization of shoes or other surfaces in contact with a floor. The sanitizing mat functions by spraying a sanitizing liquid onto the feet of a user in response to the user standing on the mat. The sanitizing mat recognizes the presence of a user by using a sensor. Once the presence of a user is detected, the sanitizing mat sprays the user's feet with a sanitizing fluid. In many embodiments, the sanitizing mat has an elevated grate standing surface that keeps the user from standing in a pool of liquid. The elevated mat grate standing surface also allows debris and excess liquid to fall through the grate onto a debris catching tray. After the sanitizing process is complete, the sanitizing mat provides a signal that the process is complete. The sanitizing indicator may be a sound or a light that is in communication with the electrical circuit. Once the process is complete, the user may step off of the mat.

The structure of the sanitizing mat generally has a fluid delivery system and sensors for detecting the presence of a user. The fluid delivery system has a reservoir, configured to store a sanitizing fluid, connected to a pump. The pump is used to pump sanitizing fluid to a plurality of fluid outlets. The fluid outlets are generally designed and dimensioned to spray sanitizing fluid onto a surface. The fluid outlets may be a combination of diffusers and nozzles. In particular, the pump is configured to transfer fluid from the reservoir to the fluid outlets.

The fluid delivery system is controlled by an electrical circuit that is in communication with a sensor that detects the presence of a user. In response to a user's presence, the sensor sends a signal to the electrical circuit, which activates the fluid delivery system, causing fluid to be expelled from the reservoir to the fluid outlets. The fluid exits the fluid outlet and passes through a plurality of apertures in the standing surface to contact the feet of a user. The fluid sanitizes the feet and may also cause removal of debris. The excess fluid or debris falls through the apertures in the standing surface and are collected by a tray that is beneath the standing surface. The sanitizing mat may also include a frame. The frame can be a rectangular member that has two sets of opposed edges.

The sanitizing mat may have a first bracket affixed to two side housing units and the frame. The mat also has a second bracket that opposes the first bracket. Both of these brackets have a ramp affixed to them. The sanitizing mat may also have a center column rotatably affixed to the brackets. The center column has a first face opposite a second face. The center column also has a first pair of opposing edges and a second set of opposing edges. The first set of opposing edges are affixed to the brackets and the second set of opposing edges are attached to a first and a second grate.

The first and second grate are configured to support the feet of a user standing on the grates. Each grate has a bottom face and a top face. The grates have a plurality of apertures that allow fluid to pass through the grates. The grates also have fluid outlets connected to the bottom faces of the grates. These fluid outlets are a combination of nozzles configured to spray a stream of liquid onto the feet of the user, and diffusers configured to spray a mist onto the feet of the user.

The sanitizing mat has at least one sensor that detects the presence of a user. Once the sensor detects the presence of a user the sensor sends a signal to an electrical circuit which activates the pump, causing fluid to be pumped from the reservoir to the fluid outlets.

Because the fluid sprayed onto the foot of a user may result in fluid and debris falling from the user's foot, the sanitizing mat may include a removable tray configured to catch debris or liquid. The removable tray is located opposite the bottom face of the grates.

The sanitizing mat further has a first side housing member and a second side housing member configured to receive the pump, the reservoir, or the electrical circuit. The side housing members are affixed to the brackets, with each side housing further comprising a first and a second compartment. Each of these compartments may have a side door pivotally attached.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6 illustrates several views of the sanitizing floor mat's nozzle rails and nozzles.

FIG. 7 illustrates a top view of the sanitizing floor mat without side housings or ramps.

FIG. 9 illustrates a bottom view of the sanitizing floor mat without side housings or ramps.

DETAILED DESCRIPTION

The invention is to a sanitizing floor mat 100 as shown in FIGS. 1-37 and a method of using the sanitizing floor mat system for sanitizing feet or surfaces in contact with the floor. Specifically, the invention is to a sanitizing floor mat system that is an improvement of traditional sanitizing floor mats that have the user step into a pool of sanitizing liquid. The instant sanitizing floor mat is designed such that a sanitizing fluid can be delivered to a user's feet without having the user stand in a pool of liquid. Additionally the sanitizing floor mat allows any debris on the feet of the user to fall into a tray, instead of back into the pool of sanitizing liquid.

Figure 12:
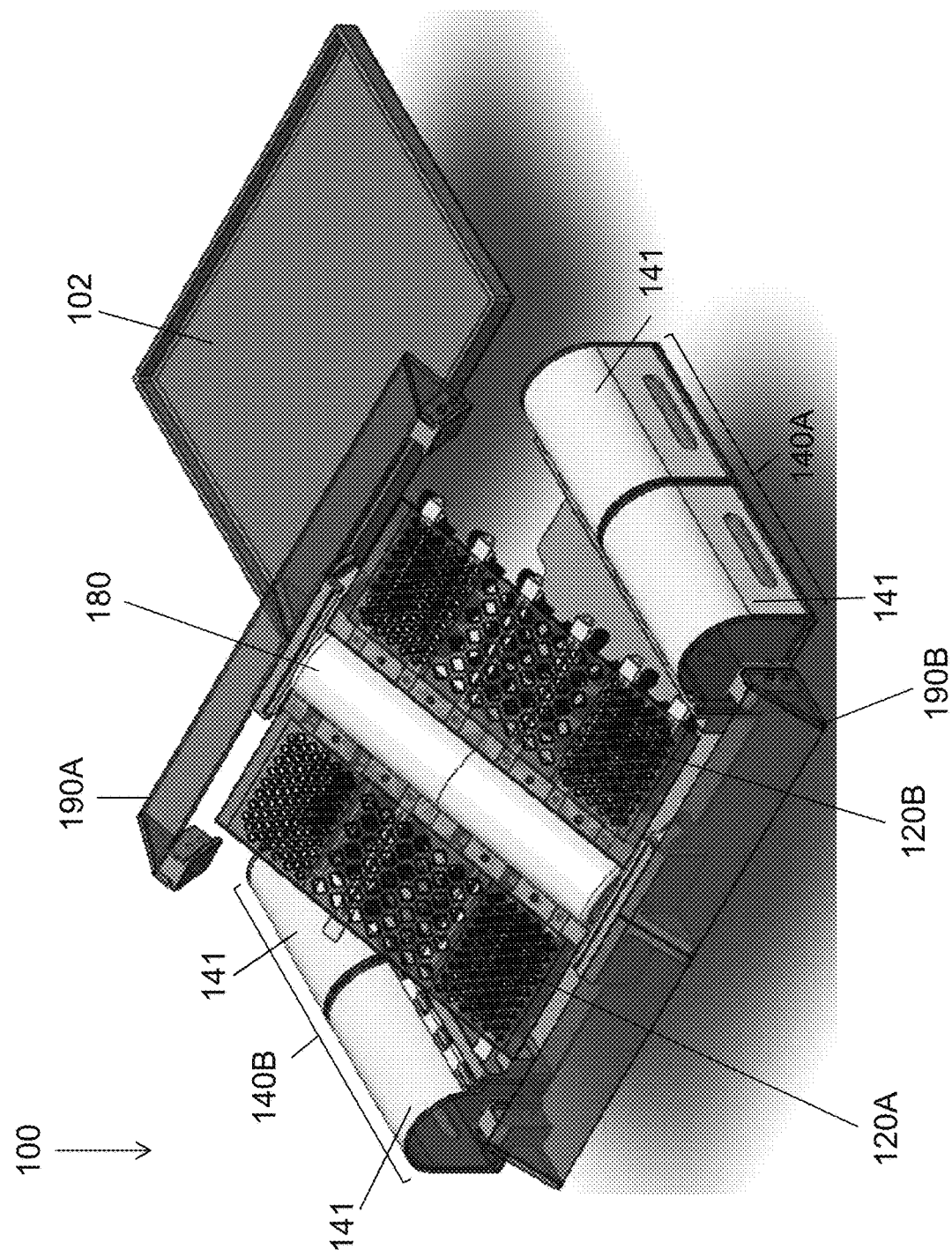
FIG. 12 illustrates a first view of the sanitizing floor mat in an open disposition.
Figure 13:
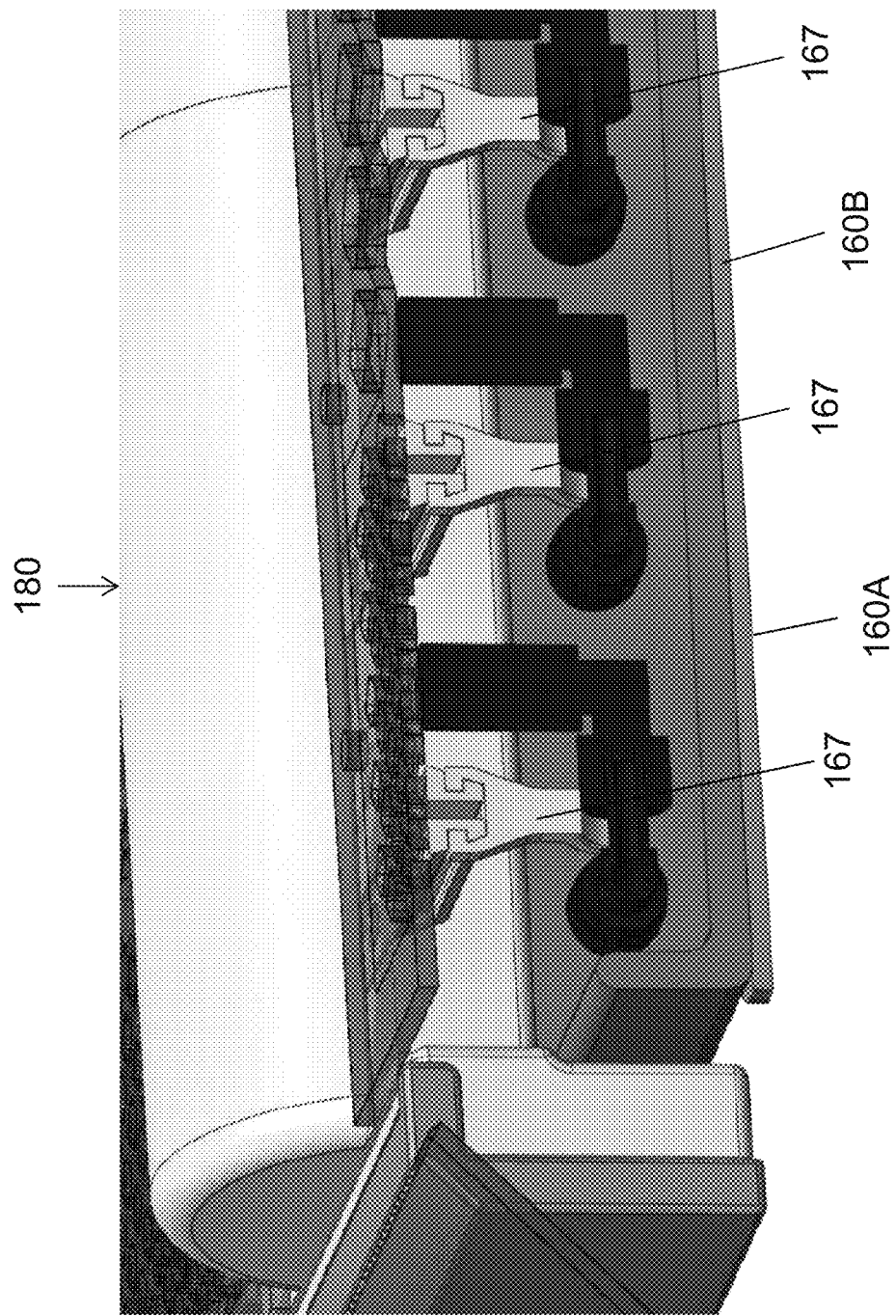
FIG. 13 illustrates a cut away view of the sanitizing floor mat showing the nozzles and nozzle rails.
Figure 14:
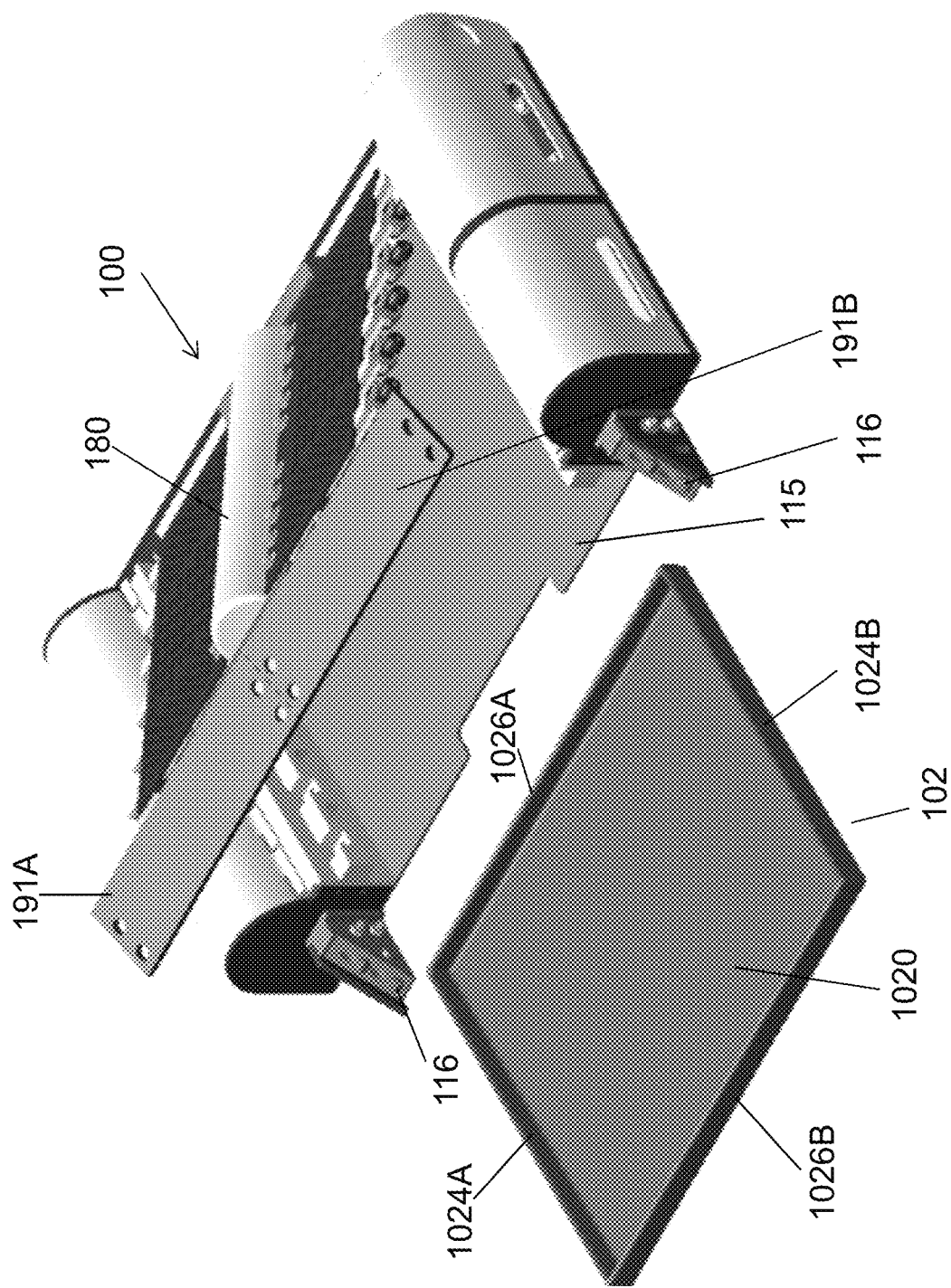
FIG. 14 illustrates a second view of the sanitizing floor mat in an open disposition.

The sanitizing floor mat 100 has a base 115 that supports the sanitizing floor mat 100. For example as shown in FIGS. 12 and 14, the sanitizing floor mat 100 may have a collection tray 102 that is configured to collect any debris or fluid that results from the foot being sprayed with a sanitizing fluid. Grates 120A-B attached to the center column 180 are configured for a user to stand on the grates 120A-B. The sanitizing floor mat 100 additionally has a side housing 140A-B. The side housing 140A-B is configured to hold a pump 150, a fluid reservoir 152, and electronics 154. Beneath the grate 120A-B, the sanitizing floor mat 100 has a plurality of fluid outlets 160. The fluid outlets 160 are attached to the grate 120A-B using one or more ribs 162. Additionally, the sanitizing floor mat 100 may have a center column 180. The center column 180 is attached to ramps 190A-B using ramp connectors 192A-B and corner brackets 116A-D. The center column 180 is attached to the standing surface 120 via grate connections 184 that receive grate bolts 188.

The sanitizing floor mat 100 may have a frame that has a rectangular configuration. Because the frame provides support for the sanitizing floor mat, the frame is a made of a material that is rigid enough to provide support. The frame 110 may be made of a rigid or semi-rigid material such as a metal or a plastic, or a combination of metals and plastics. The frame 110 preferably has a rectangular shape, but other shapes such as square could be selected. The frame also has a top face 1101 and a bottom face 1102. The bottom face 1102 of the frame is configured to rest on the floor, supporting the other components of the sanitizing floor mat 100. The frame's edges may be configured to engage a set of brackets. The frame may include a base. For example as shown in FIG. 12, the base 115 may be a sheet of rigid material that rests between both sets of the frame's opposing edges. Like the bottom face of the frame, the bottom face of the base is configured to be in contact with the floor. The base 115 may be attached to each edge of the frame 110. The frame 110 may have only one set of opposing edges that are connected by the base 115. One of skill in the art will appreciate that the frame 110 may have any suitable shape, including a square or triangle. The frame should have dimensions that are appropriate for accommodating various sizes of user feet. As a non-limiting example, the frame may be a 24 inch by 15 inch rectangle. The frame may also be a 30 inch by 20 inch rectangle.

Figure 18:
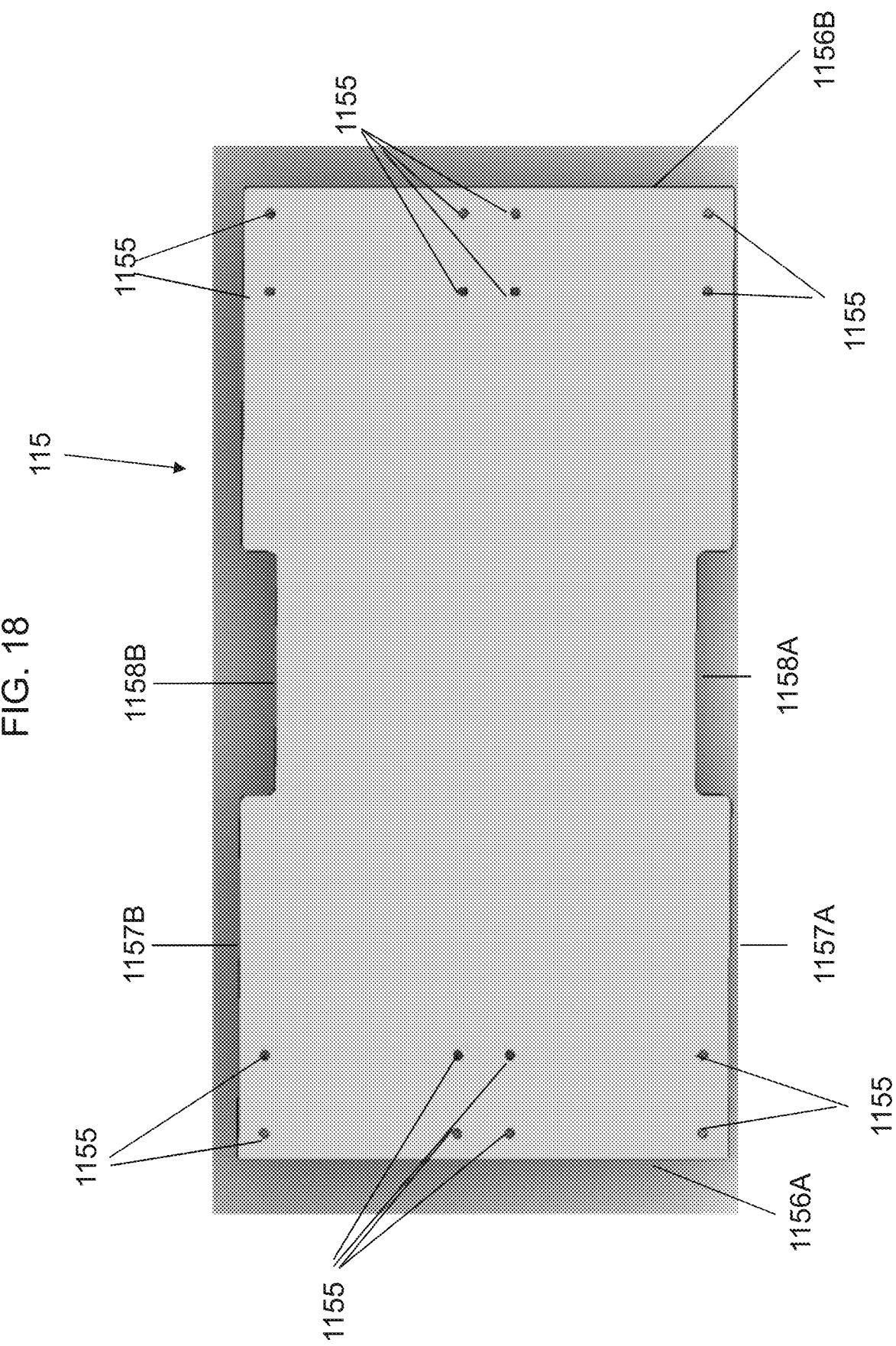
FIG. 18 illustrates the base plate of the sanitizing mat.

The base 115 has a top face 1152 and a bottom face 1154. For example as shown in FIG. 18, the base is a rectangular sheet that has a first set of edges 1156A-B and a second pair of opposing edges 1157A-B. Both edges of the second set of opposing edges 1157A-B, may have rectangular notches 1158A-B near the center of the second set of opposing edges 1157A-B. The bottom face 1154 is configured to rest on a floor or other similar surfaces. The base may be configured to receive a tray 102 on the top face 1152 of the base 115. The base 115 has a plurality of apertures 1155 that are configured to accept screws, bolts, or other fasteners for securing components of the sanitizing mat 100 thereto. One of skill in the art will appreciate that the base 115 may have any suitable shape, including circle, square, or triangle.

The sanitizing mat 100 may have side housings 140A-B attached to it. In this regard, the side housings 140A-B act as a frame for constructing the sanitizing mat 100. For example as shown in FIGS. 21-26, each side housing 140A-B may be made of two side housing sections 141A-D. The side housing sections 141A-D may consist of a side housing base 146, a side housing bracket 1400, a pair of opposing side housing walls 147A-B, and a U-shaped side housing door 142. Each side housing base 146 is a rectangular sheet that has a first set of edges 1460A-B and a second pair of opposing edges 1462A-B. The side housing base 146 has a top face 1464 and a bottom face 1466. The side housing base 146 has a plurality of apertures 1469 for accepting screws, bolts, or other fasteners for securing side housing base 146 to the sanitizing mat base 115. The side housing base 146 may also have a plurality of apertures 1468A-C for accepting protrusions 1440A-C from a side housing bracket 1400. The side housing walls 147A-B have a curved top edge 1471 opposite a flat bottom edge 1470. The side housing walls 147A-B also have a pair of parallel straight edges 1472 and 1473 opposite each other. The side housing walls 147A-B also may have a minor edge 1475 that is opposite and parallel to the flat bottom edge 1470. The first edge 1472 joins the curved top 1471 and the flat bottom 1470. The second edge 1473 joins the minor edge 1475 and the bottom edge 1470. The top of the side housing walls 147A-B may have a curve that has the same radius as the U-shaped door 142. The side housing wall 147 may also include apertures 1478A-B configured to accept screws, bolts, or other fasteners for securing the side housing wall 147 to a corner bracket 116. The side housing wall 147 may also include apertures 1479A-B configured to accept side housing bracket protrusions 1402. One of skill in the art will appreciate that the side housings 140A-B and side housing sections may have any shape that is suitable for housing a pump 150, a reservoir 152, or an electrical circuit 154.

Figure 26:
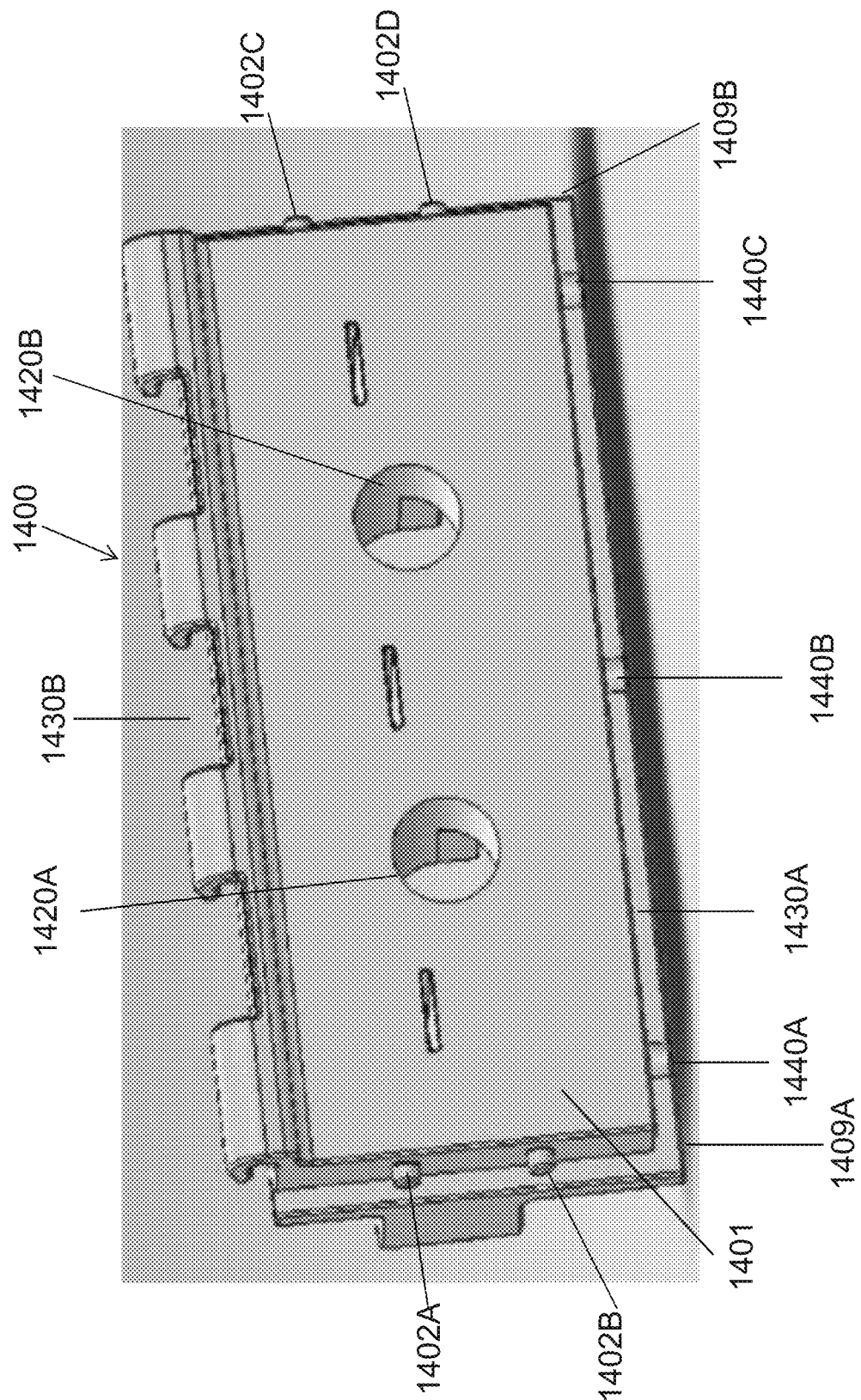
FIG. 26 illustrates a second view of the side housing bracket.

The side housing bases 146 are affixed to the sanitizing mat base 115 with the bottom face 1466 of the side housing base 146 opposite the top face 1152 of the sanitizing mat base 115. The side housing bracket 1400 is a rectangular member that has a first set of opposing edges 1409A-B and a second pair of opposing edges 1430A-B. The side housing bracket 1400 also has a first face 1401 and a second face 1403. For example as shown in FIG. 26, the side housing bracket 1400 has a second set of edges 1430A-B. Of the second set of opposing edges 1430A-B, a base edge 1430A has a plurality of protrusions 1440A-C configured to be accepted by the bracket apertures 1468A-C in the side housing base 146. The side housing bracket 1400 is affixed to the side housing base 146 by inserting the bracket protrusions 1440A-C into the bracket apertures 1468A-C. This allows the side housing bracket 1400 to be perpendicular to the side housing base 146. Of the second set of opposing edges 1430A-B, a hinge edge 1430B has a configuration that is hingedly attached to the side housing door 142. Each edge of the first set of opposing edges 1409A-B has protrusions 1402 that are configured to be accepted by the apertures 1479A-B in the side housing walls 147A-B. The side housing bracket 1400 may also have a plurality of apertures 1420A-B for allowing fluid lines to connect the fluid delivery system components held inside the side housings to fluid outlets 160 that line the bottom face of the grate 120A-B. The second face 1403 of the side housing bracket has a plurality of protrusions that are configured to act as rib acceptors 1410A-C. The rib acceptors 1410A-C may be a single protrusion.

Figure 1:
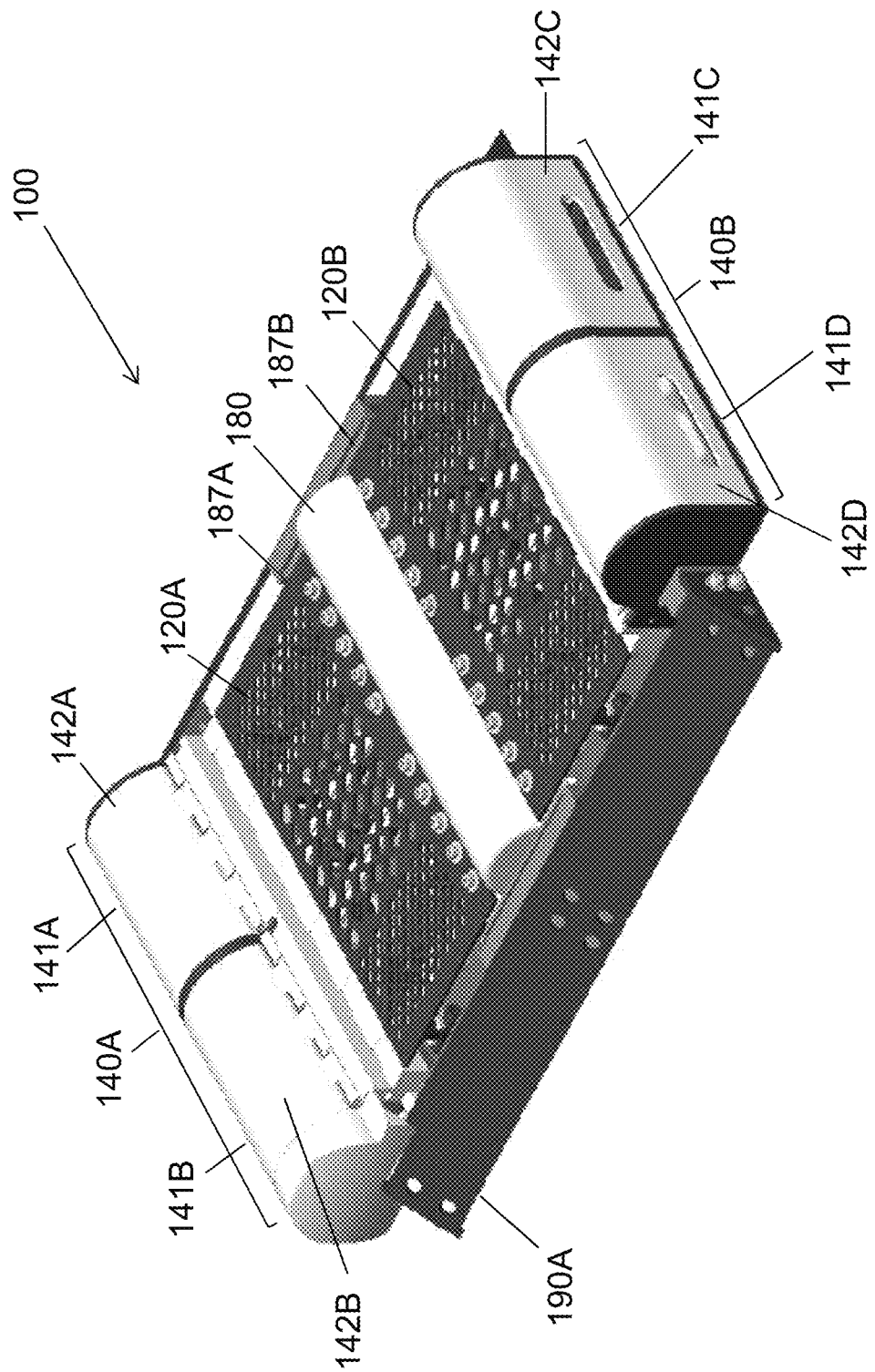
FIG. 1 illustrates a perspective view of the sanitizing floor mat in one embodiment.
Figure 2:
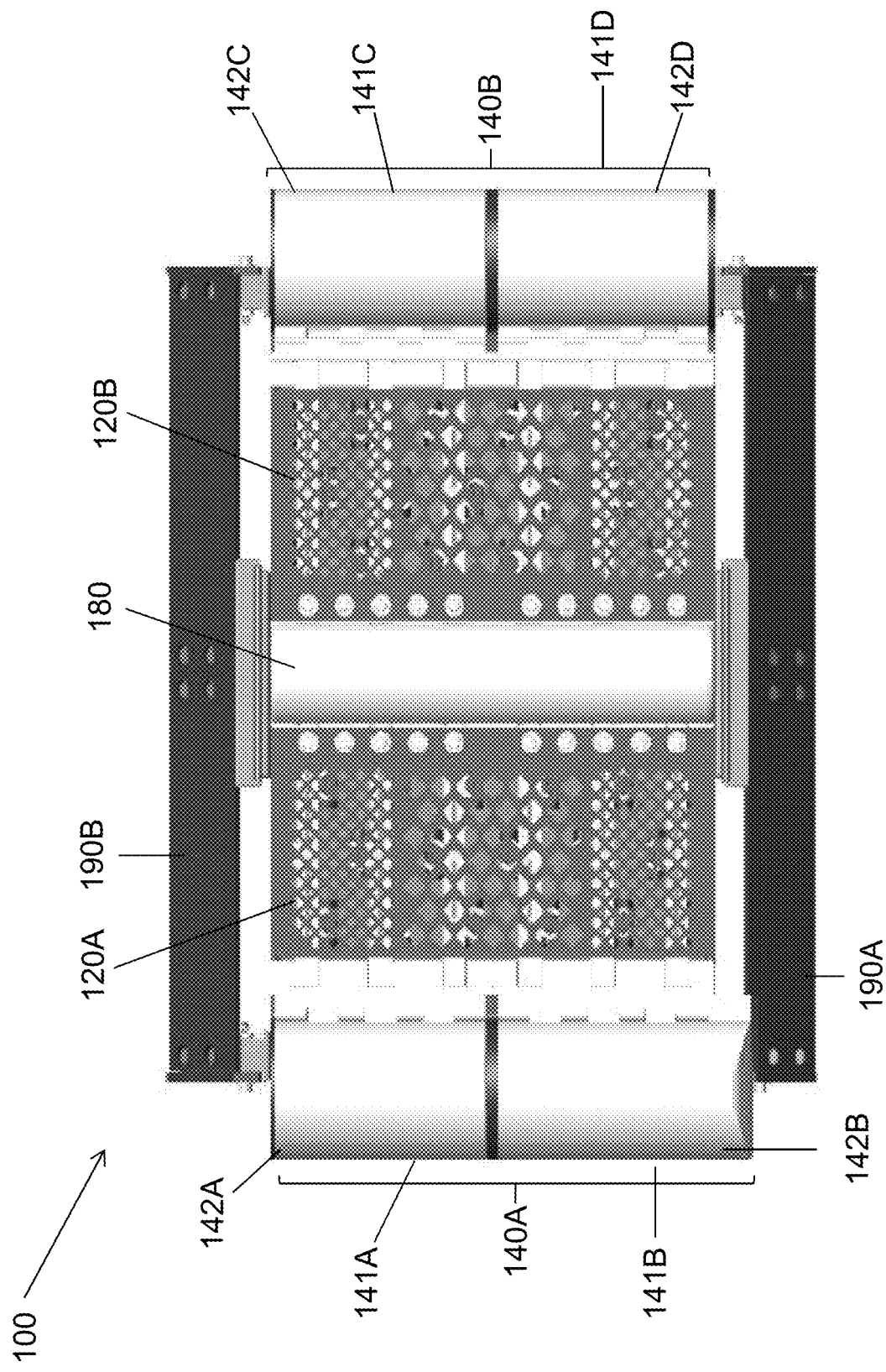
FIG. 2 illustrates a top view of the sanitizing floor mat in one embodiment.
Figure 3:
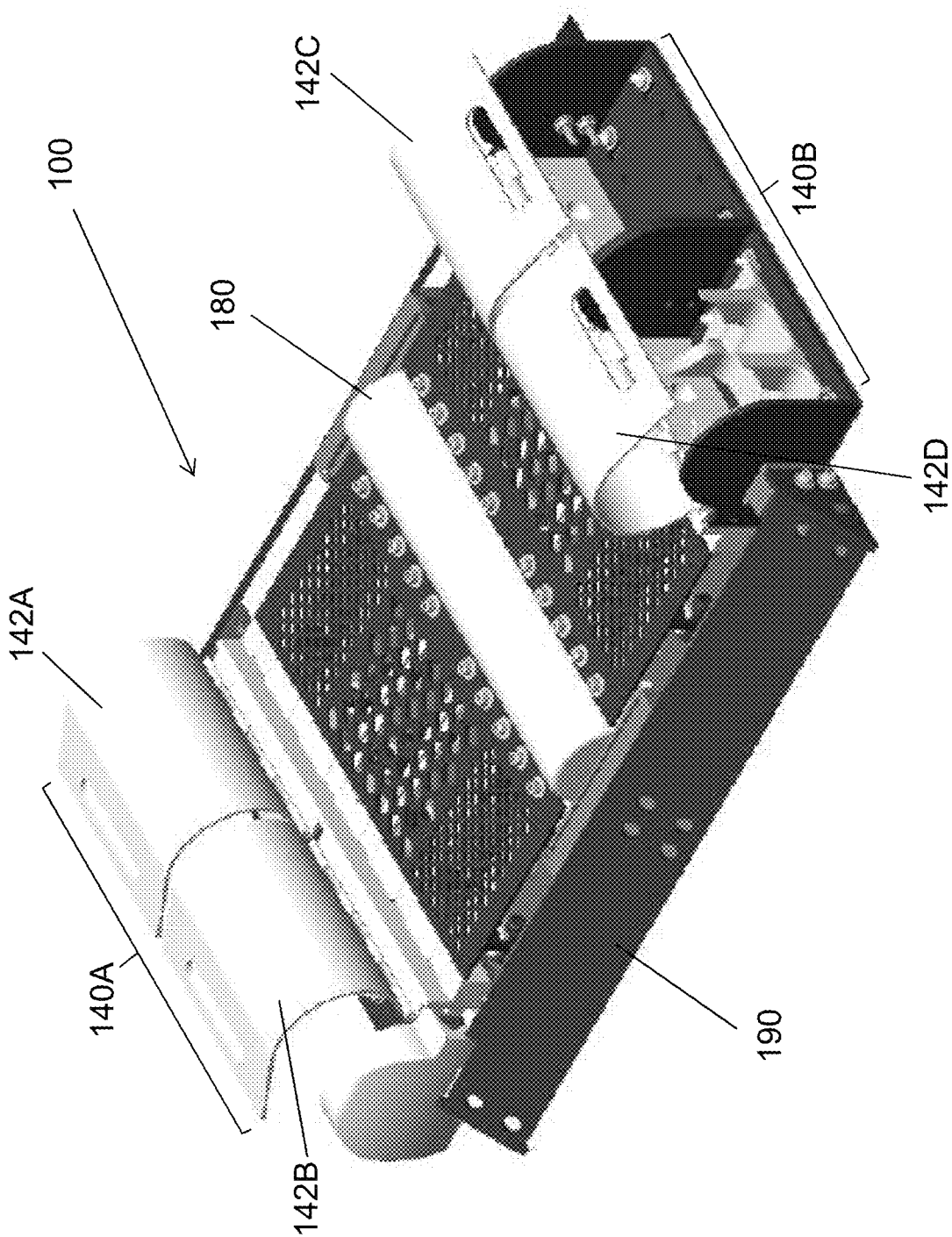
FIG. 3 illustrates a view of the sanitizing floor mat with the side housing open.
Figure 4:
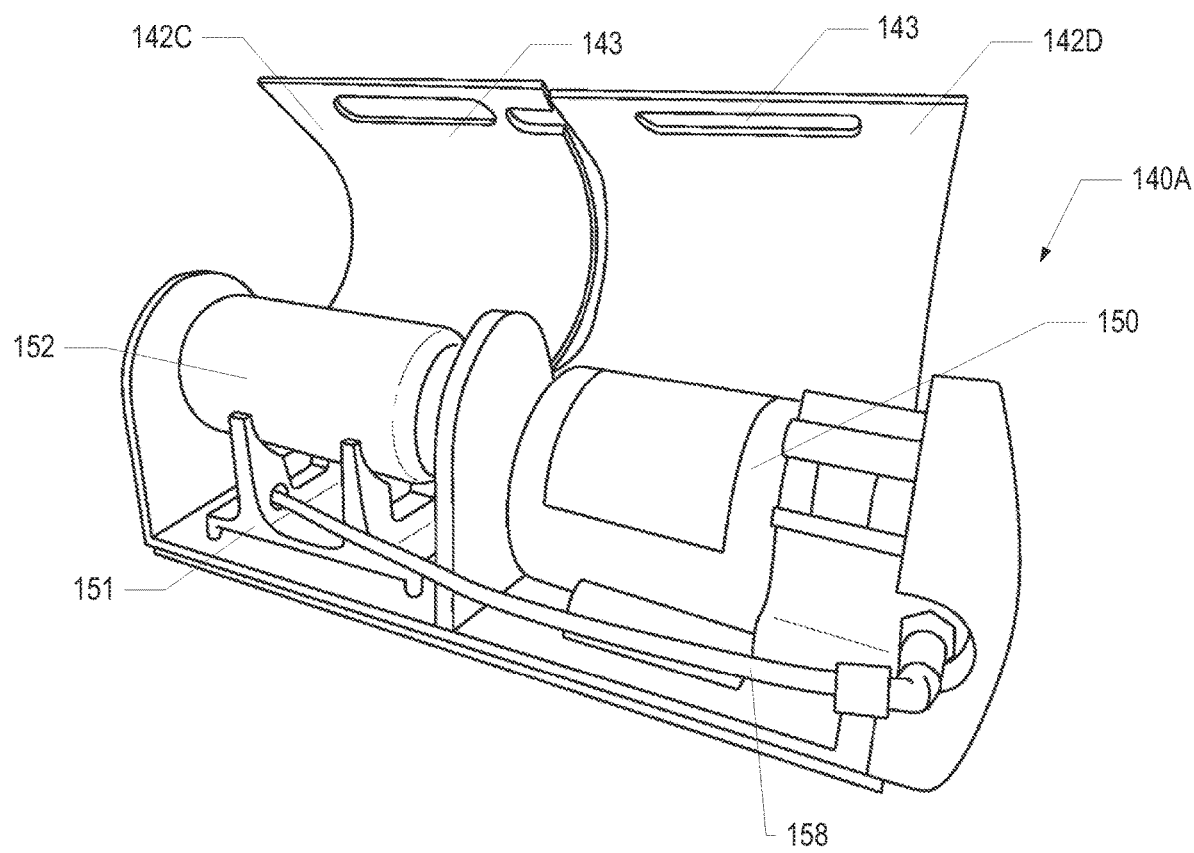
FIG. 4 illustrates a view of the sanitizing floor mat's side housing holding a reservoir and pump.
Figure 5:
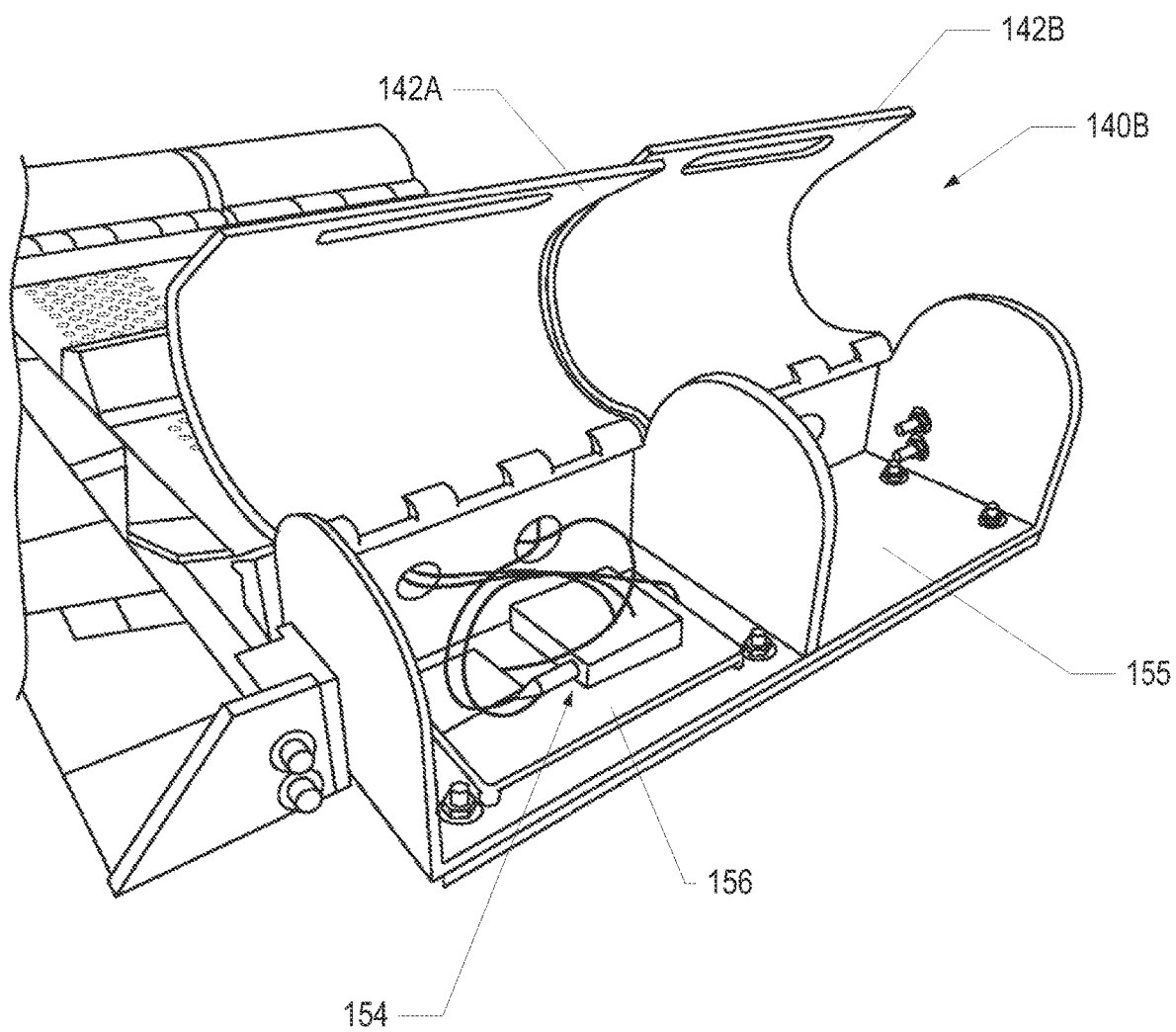
FIG. 5 illustrates a view of the sanitizing floor mat's electronic components.
Figure 27:
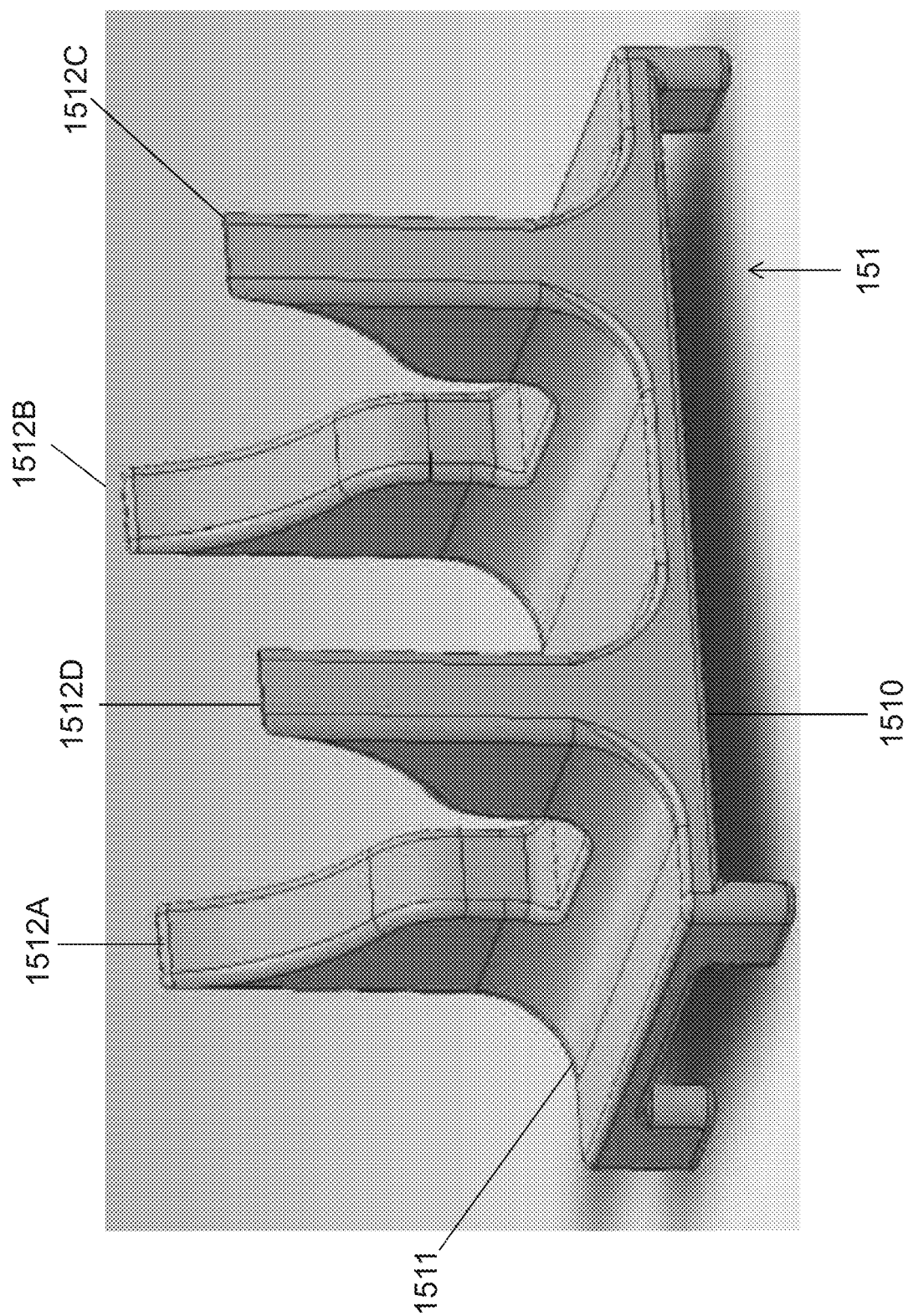
FIG. 27 illustrates a fluid reservoir holder.
Figure 28:
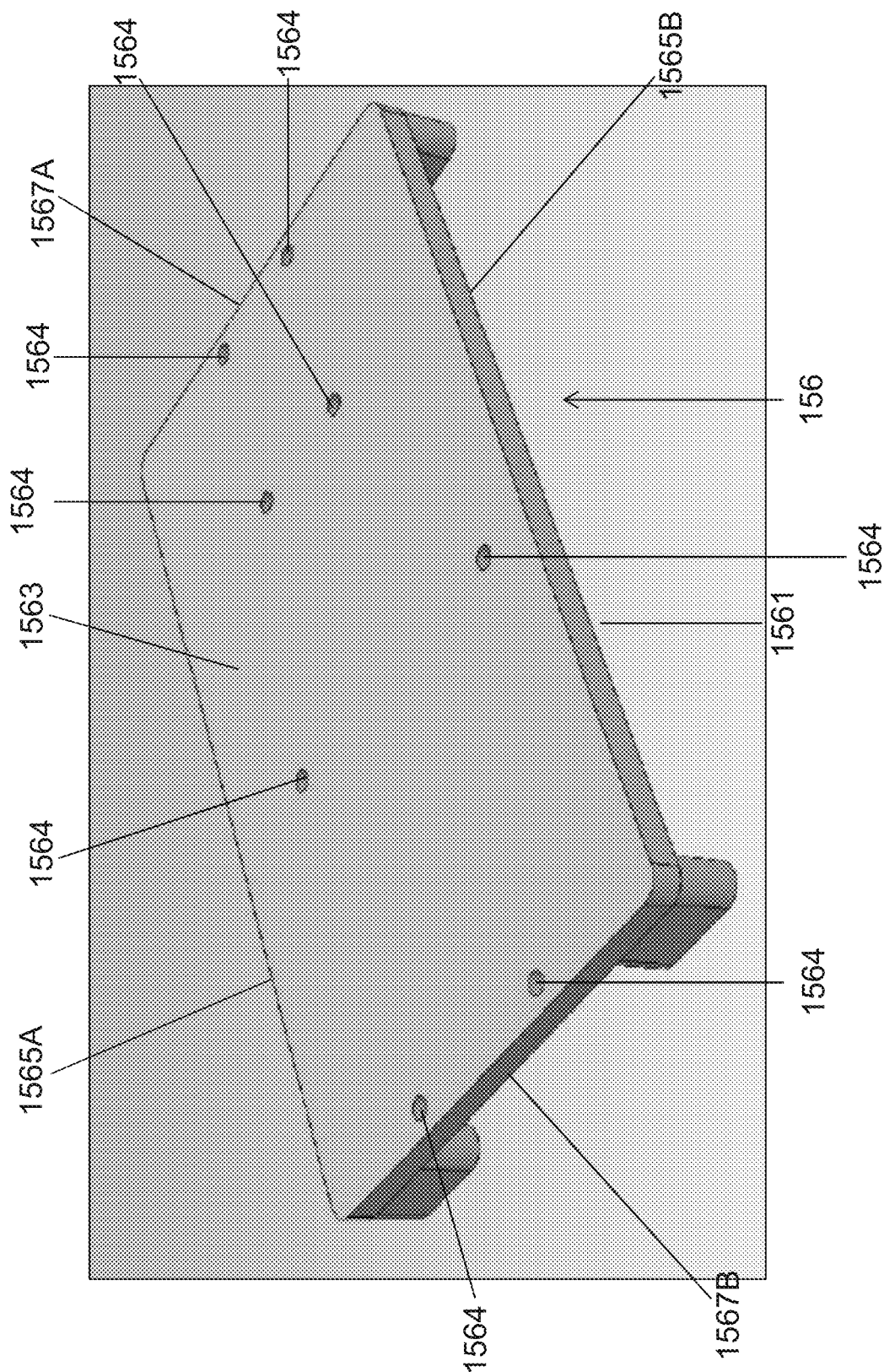
FIG. 28 illustrates an electronics holder.

Once the side housing base 146, side housing bracket 1400, the pair of opposing side housing walls 147A-B, and U-shaped side housing door 142 are assembled, the assembled side housing members 140A-B may serve two purposes, first as a frame for the sanitizing mat components, and second as a housing for various components. For example as shown in FIGS. 4-5, the side housing members 140A-B may be configured to house one or more components chosen from a group that includes, but is not limited to a pump 150, a reservoir 152, and an electrical circuit 154. Side housing member 140A-B may include a fluid reservoir holder 151 for holding a fluid reservoir. The fluid reservoir holder 151 generally as a bottom face 1510 that is opposite a top face 1511. The fluid reservoir holder 151 also has a top face that has a plurality of protrusions 1512A-D configured to hold a fluid reservoir 152. For example as shown in FIG. 27, protrusions 1512A-D may be curved to hold a cylindrical fluid reservoir. One of skill in the art will appreciate that these protrusions 1512A-D may be any shape that is capable of accepting a fluid reservoir 152. Some of the side housing members 140A-B may include electronics holders 156. The electronics holder 156 is a rectangular member that has a first set of opposing edges 1565A-B, and a second set of opposing edges 1567A-B. The electronics holder 156 has a bottom face 1561 and a top face 1563. The bottom face 1561 is secured to the top face 1563 of the side housing base 146. The top face 1563 of the electronics holder is configured to hold electronics 154 that control the sanitizing mat 100. One of skill in the art will appreciate that the side housing members 140A-B may be any shape that is appropriate for housing a fluid reservoir 152, a pump 150, or an electrical circuit 154. The side housing members 140A-B may remain empty. Each side housing member 140A-B may be attached to opposing edges of the frame 110. Each side housing member 140A-B may be a unitary housing. Each side housing member 140A-B may be divided into two or more side housing sections 141A-D. The doors 142A-D of the side housing members may be rotatably attached to the side housing sections 141A-D. The side housing doors 142A-D are attached to the side housing by inserting the hinge rod 144 through the side housing hinge 144S. The doors of the side housing members 140A-B provide an access point to the reservoir 152, pump 150, or electrical circuit 154 held inside the side housing member. The side housing doors 142A-D may have apertures that act as side housing door handles 143. The pump 150 and the fluid reservoir 152 are in communication with one another. The pump 150 and the reservoir 152 are also in fluid communication with the fluid outlets 160. The side housing 140A-B is configured to allow the fluid reservoir 152 and the pump 150 to be in fluid communication with one another. The side housing 140A-B is also configured to allow the electrical circuit 154 to communicate with the pump 150 and the reservoir 152. The side housings 140A-B may be made of plastic or some other rigid or semi-rigid material. In other embodiments, the side housing 140A-B may be made of a metal. By way of non-limiting example, the side housing sections 141A-D may have a height of about 5 inches and a width of about 5 inches. One of skill in the art will appreciate that the side housings 140A-B and side housing sections 141A-D may have dimensions that are appropriate for housing a pump 150, reservoir 152, or electrical circuit 154.

Figure 37:
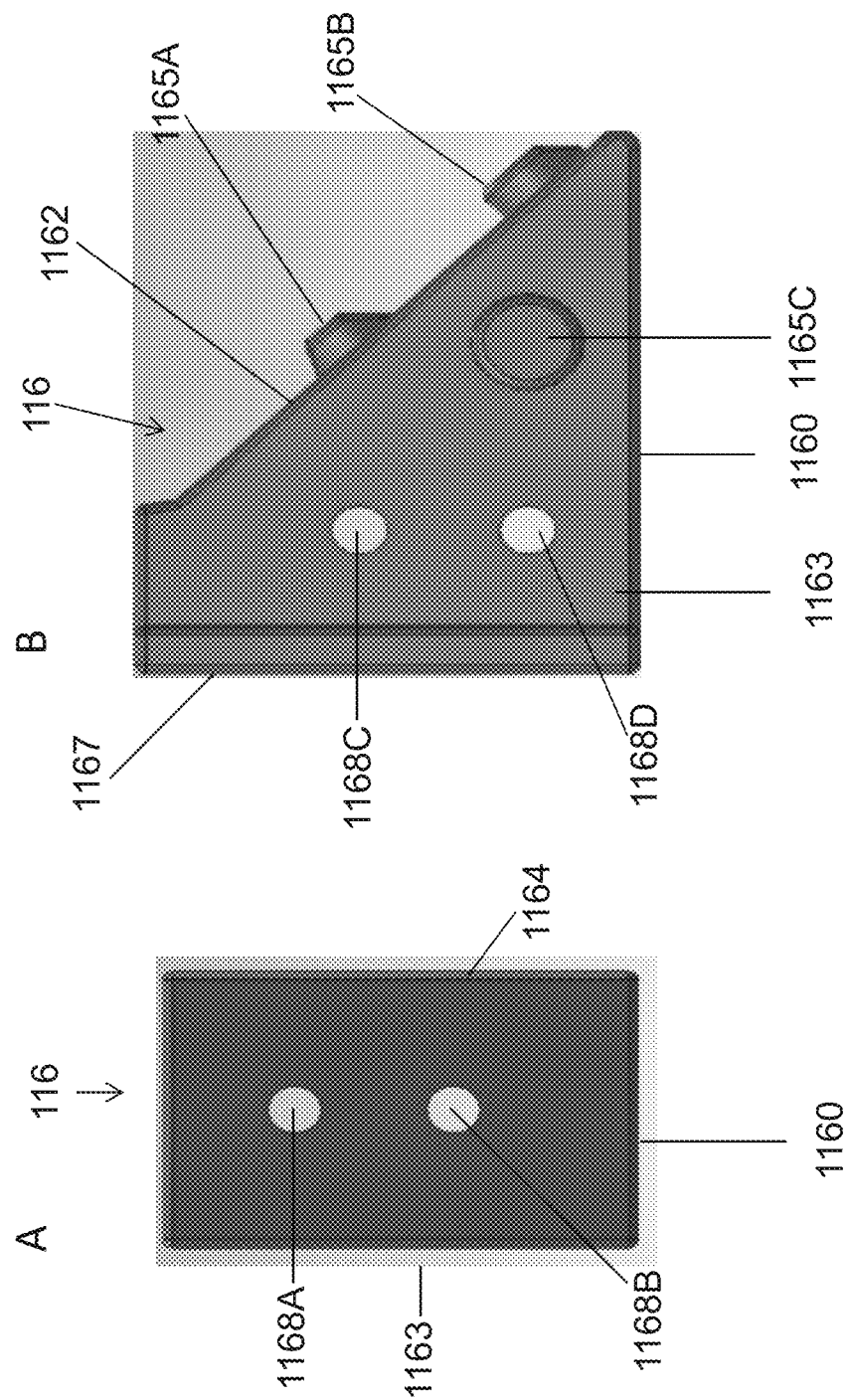
FIG. 37 illustrates a center bracket connecter.
Figure 37:
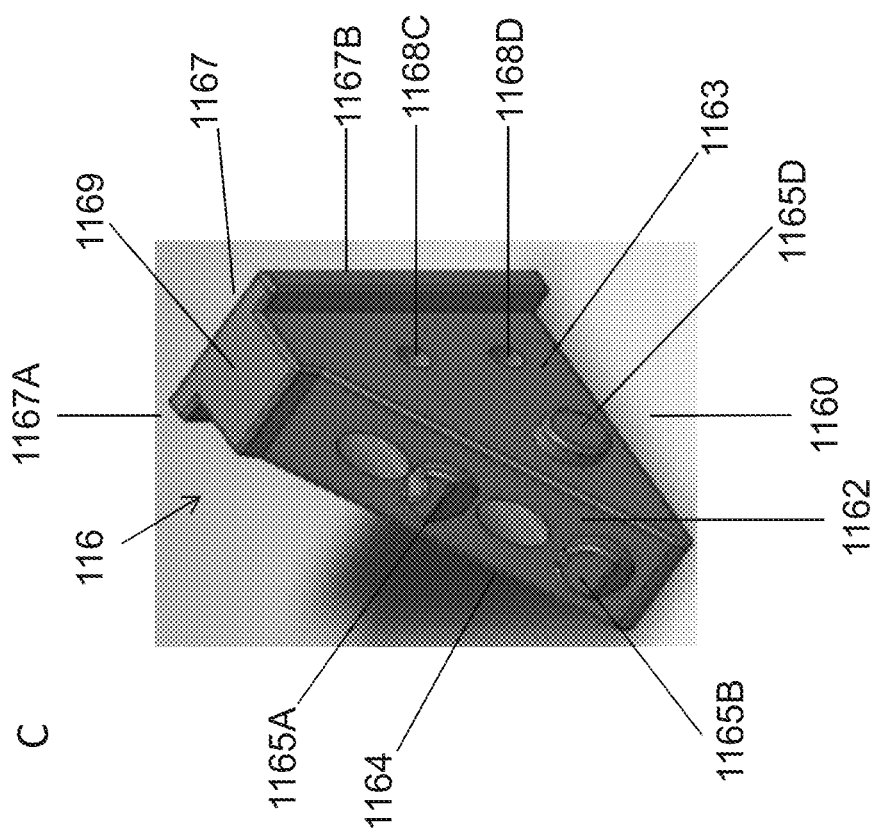

The side housing walls 147 may have corner brackets 116 attached thereto. These corner brackets 116A-D may have a triangular shape. For example as shown in FIG. 14 and FIG. 37, each corner bracket 116A-D may have a front face 1162, a bottom face 1160, a rear face 1167, an inner face 1163, and an outer face 1164. Each corner bracket 116A-D may have inner faces 1163 and outer faces 1164 that oppose each other. The corner brackets 116A-D may also include a flat top face 1169 opposite the bottom face 1160. Additionally, the rear face 1167 may extend beyond the inner face 1163 and outer face 1164 to form a pair of flanges 1167A-B. The front 1162, bottom 1160, and rear faces 1167 of the corner brackets 116A-D may meet one another to form a triangle. The corner brackets 116A-D may also have a first set of apertures 1168A-B through the front face 1162 and the rear face 1167. These apertures 1168A-B are configured to receive screws, bolts, or other fasteners for securing the side housing wall 147A-B. The corner brackets 116A-D may also have a second set of apertures 1168 C-D that run through the inner face 1163 and outer face 1164. The inner 1163 and outer faces 1164 of the corner brackets may also include protrusions 1165C-D.

The corner bracket's rear face 1167 is attached to the side housing wall 147A-B using a fastener. The front face 1162 of the corner brackets 116A-D may include a pair of protrusions 1165 that are configured to be accepted by a ramp member apertures 1915. The front faces 1162 of the corner brackets 116A-D may be slanted. One of skill in the art will appreciate that the corner brackets 116A-D may have any shape known in the art for attaching members to one another in different planes. The corner brackets 116A-D may be made of steel, aluminum, or hard plastic. One of skill in the art will appreciate that the corner brackets 116A-D may be made of any material known the art.

Figure 29:
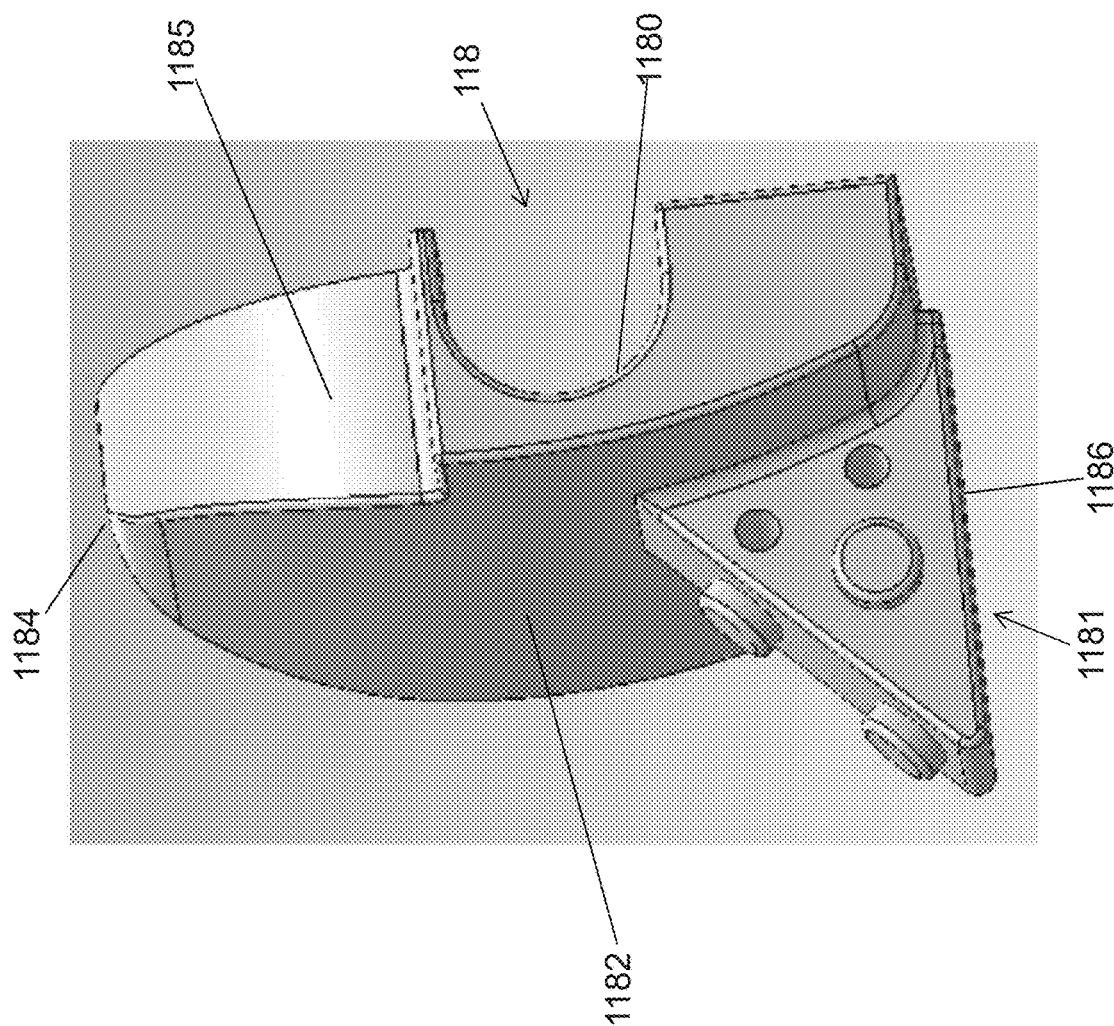
FIG. 29 illustrates a pump ramp corner.
Figure 30:
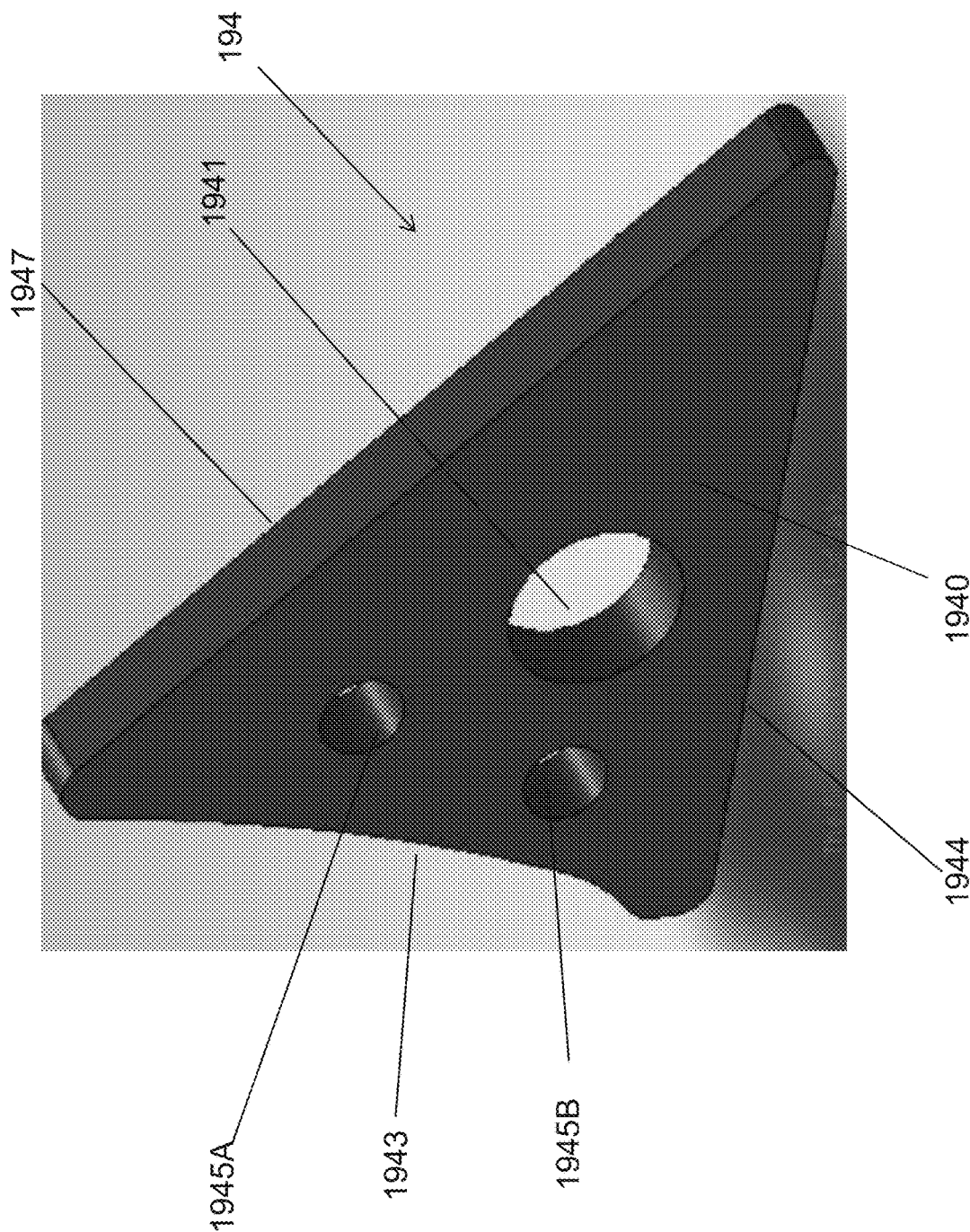
FIG. 30 illustrates a side for a pump ramp corner.

The sanitizing mat 100 may also include a pump holder 118. The pump holder 118 is configured to hold a pump 150 inside of a side housing section 141. For example as seen in FIG. 29, the pump holder 118 has a bracket section 1181. The pump holder 118 has an inner face 1180 opposite an outer face 1182. The pump holder 118 also has a top face 1184 opposite a bottom face 1186. The pump holder 118 also has a pair of side faces 1185A-B opposite one another. The bracket portion 1181 of the pump holder 118 is configured to perform the same function as the other corner brackets 116. The pump holder 118 may replace a wall 147 of one of the side housing sections 141.

The sanitizing mat 100 may include a center column 180. The center column 180 may act as center support for a standing surface 120A-B. For example as shown in FIGS. 7-10 and FIG. 20, the center column 180 may have a bottom face 1802 opposite a curved top face 1801. The center column 180 may have a first pair of opposing edges 183A-B and a second set of opposing edges 184A-B. The second set of edges 184A-B are flanges that include a plurality of apertures 1841A-H configured to accept screws, bolts, or other fasteners for securing center column 180 to the standing surface 120A-B. The first set of opposing edges 183A-B may be configured to be attached to ramp connectors 192A-B. The first set of edges 183A-B may include apertures 1805 configured to accept screws, bolts, or other fasteners for securing center column to ramp connectors 192A-B. These ramp connectors 192A-B are configured to communicate with center ramp brackets 193A-B.

Each center ramp bracket 193A-B may have a pair of side faces 1935 that oppose each other. The center ramp brackets 193A-B may also include a bottom face 1930, a front face 1931, and a rear face 1933. The front 1931, bottom 1930, and rear faces 1933 of the center ramp brackets 193A-B may meet one another to form a triangle. Additionally, the front face 1931 may include a pair of apertures 1932A-B configured to receive screws, bolts, or other fasteners for securing ramp members 191A-B and ramp connectors 192A-B and center column connector 197A-B.

Figure 35:
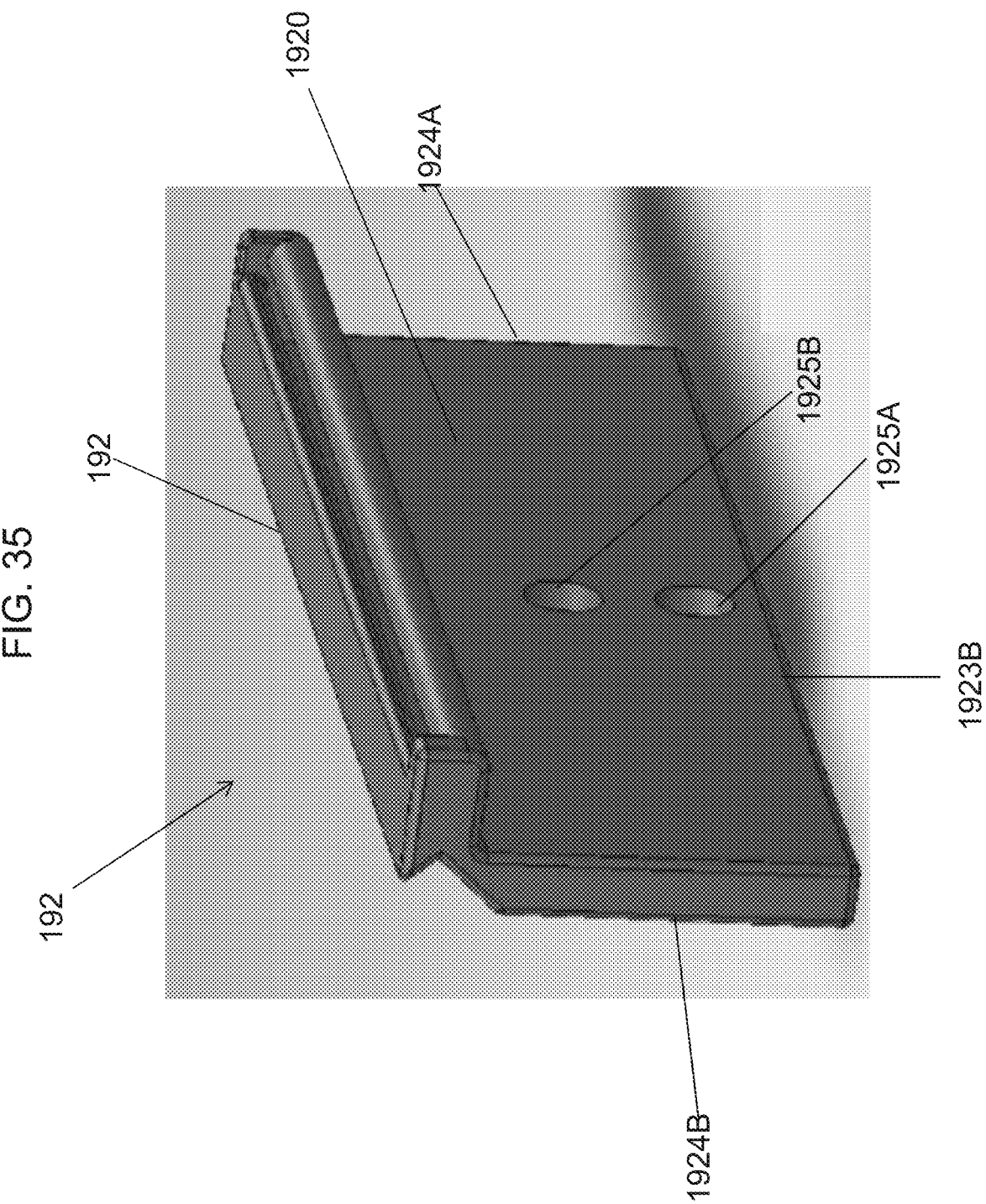
FIG. 35 illustrates a center ramp bracket.

The ramp connectors 192, as shown in FIG. 35, are rectangular members that have an inner face 1920, a rear face 1921, a first set of opposing edges 1923A-B, and a second set of opposing edges 1924A-B. The ramp connectors 192A-B also may include a plurality of apertures 1925A-B configured to receive screws, bolts, or other fasteners for securing ramp members 191A-B, ramp connectors 192A-B, and center column connector 197A-B.

Figure 36:
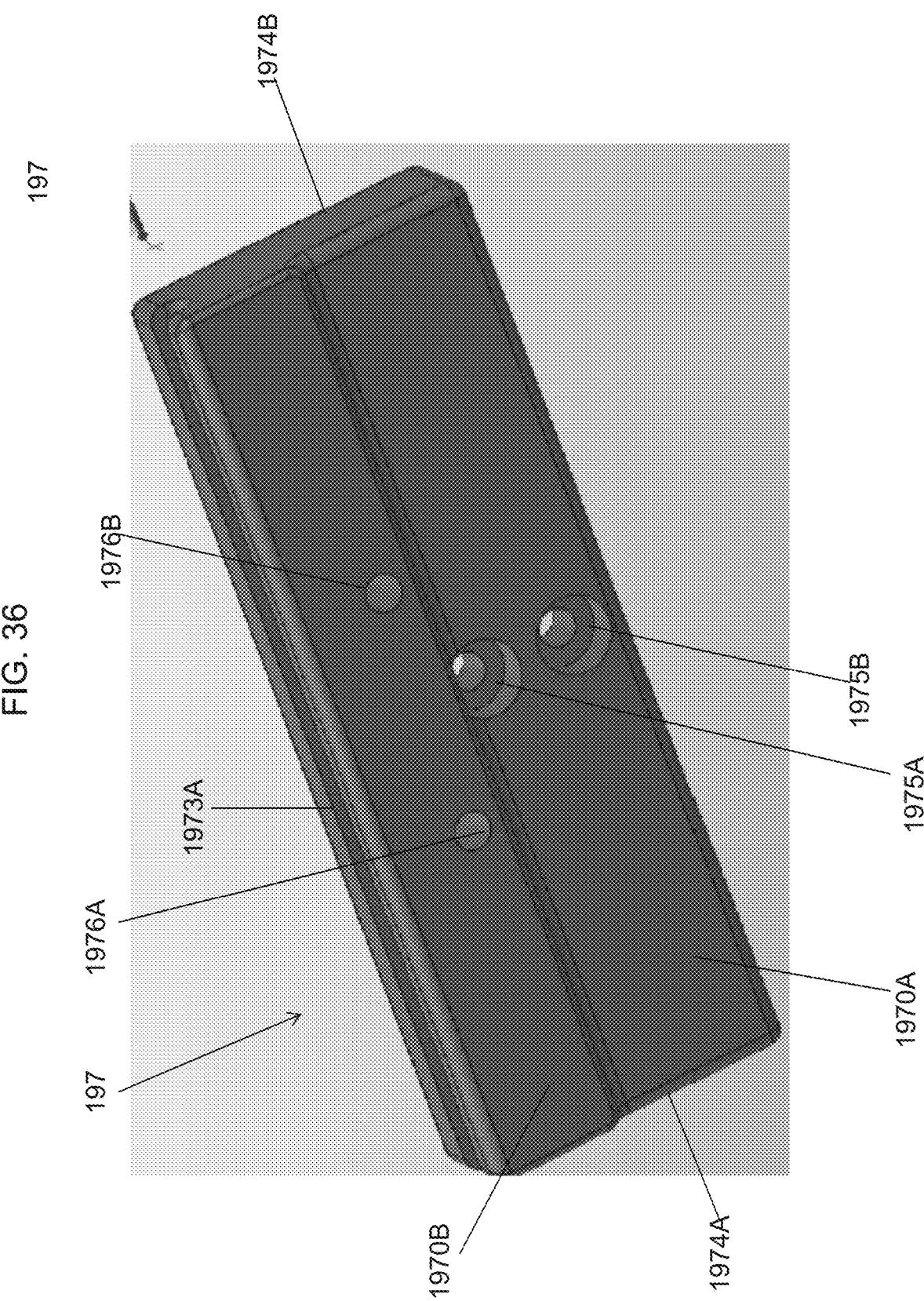
FIG. 36 illustrates a ramp connecter.

The center column connectors 197A-B, as shown in FIG. 36, are rectangular members that have an inner face 1970, a rear face 1971, a first set of opposing edges 1973A-B, and a second set of opposing edges 1974A-B. The inner face may have two planes, a lower plane 1970A and an upper plane 1970B. The center column connectors 197A-B also may include a plurality of apertures 1975A-B configured to receive screws, bolts, or other fasteners for securing ramp members 191A-B and ramp connectors 192A-B and center column connector 197A-B. The center column connectors 197A-B may also include apertures 1976A-B, for accepting protrusions 1934A-D from the center ramp brackets 193A-B.

The center ramp brackets 193A-B have a front face that is configured to be attached to a ramp member 190. The ramp connectors 192A-B may be rotatably attached to the center ramp brackets 193A-B. One or both of the ramp connectors 192A-B may be removably attached to the center ramp brackets 193A-B. When the sanitizing mat 100 is in a closed disposition, the center ramp connectors 192A-B are coplanar with the front faces 1162 of the corner brackets 116. In this regard, the center ramp connectors 192A-B and the front faces 1162 of the corner brackets 116 are all configured to receive a ramp member 190A-B. The center ramp brackets 193A-B and the ramp connecters 192A-B may be made from a metal or a hard plastic. One of skill in the art will appreciate that the center ramp brackets 193A-B and the ramp connecters 192A-B may be made of any suitable material.

The pump 150 and the reservoir 152 are in fluid communication with the fluid outlets 160 to form a fluid delivery system. The fluid delivery system may be controlled by the electrical circuit 154. The electrical circuit 154 may be configured to receive a signal from the sensor and respond to the signal by making the fluid delivery system pump fluid from the reservoir 152 to the fluid outlets 160.

The sanitizing mat 100 may include a ramp member 190A-B for aiding a user in stepping onto the standing surface without tripping. The ramp member 190A-B may be two rectangular ramp sections 191A-B. Each ramp section 191A-B has a front face 1901A-B, a rear face 1902A-B, and a first set of opposing edges 191A-B. The ramp 190 may be fixedly attached to the center ramp connector 193A-B with the rear face 1902 of the ramp 190A-B being in contact with the center ramp connector 193. The rear face 1902 of the ramp 190A-B may be connected to the sanitizing mat 100 with the rear face 1902 of the ramp member being in direct contact with the front face 1162 of two of the corner brackets 116. The ramp 190A-B may be made of a rigid material that can support the weight of a user. In other embodiments, the ramp member 190A-B may be made of any rigid material known in the art.

Figure 31:
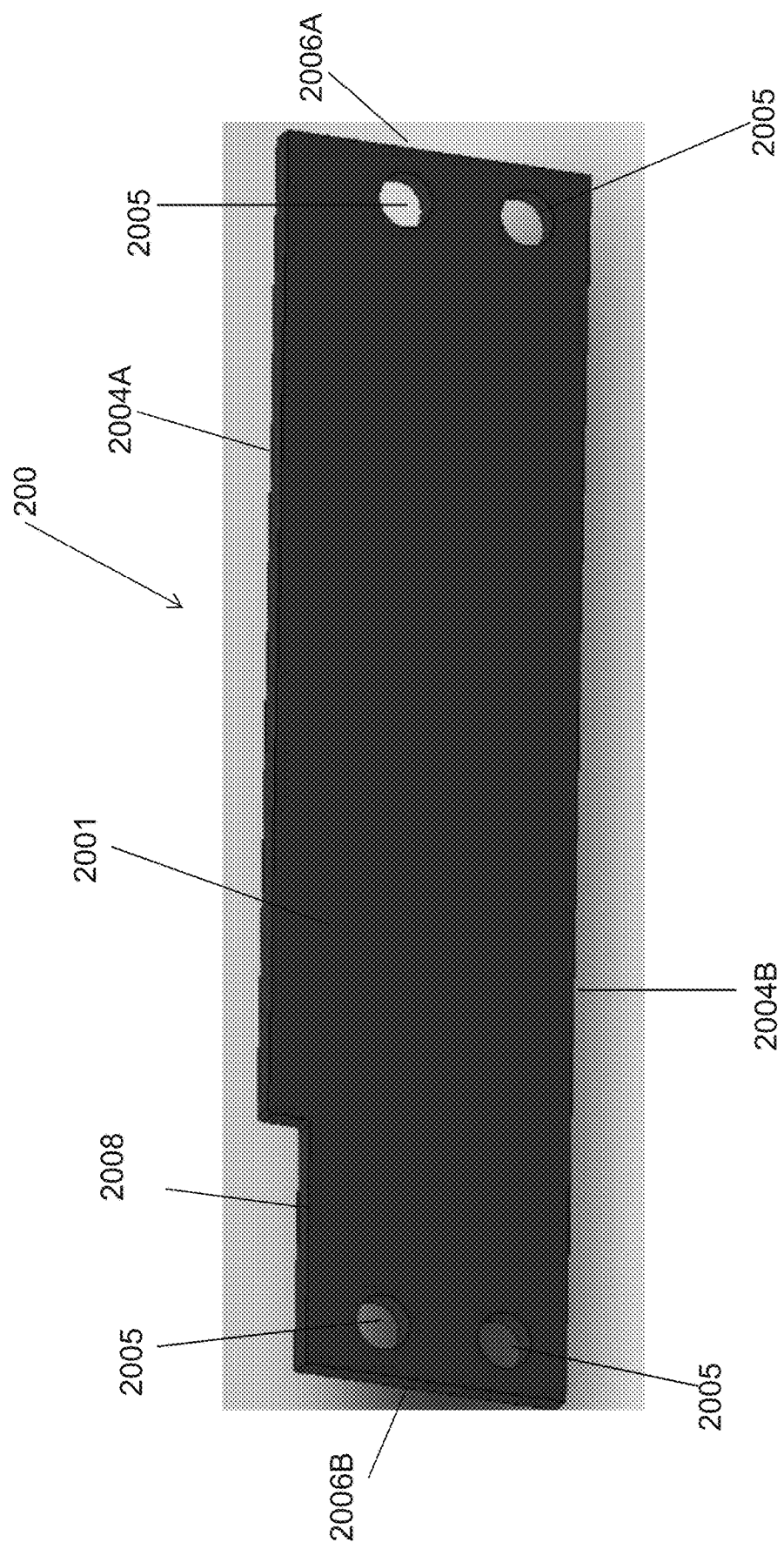
FIG. 31 illustrates a first portion of a ramp member for the pump side.
Figure 32:
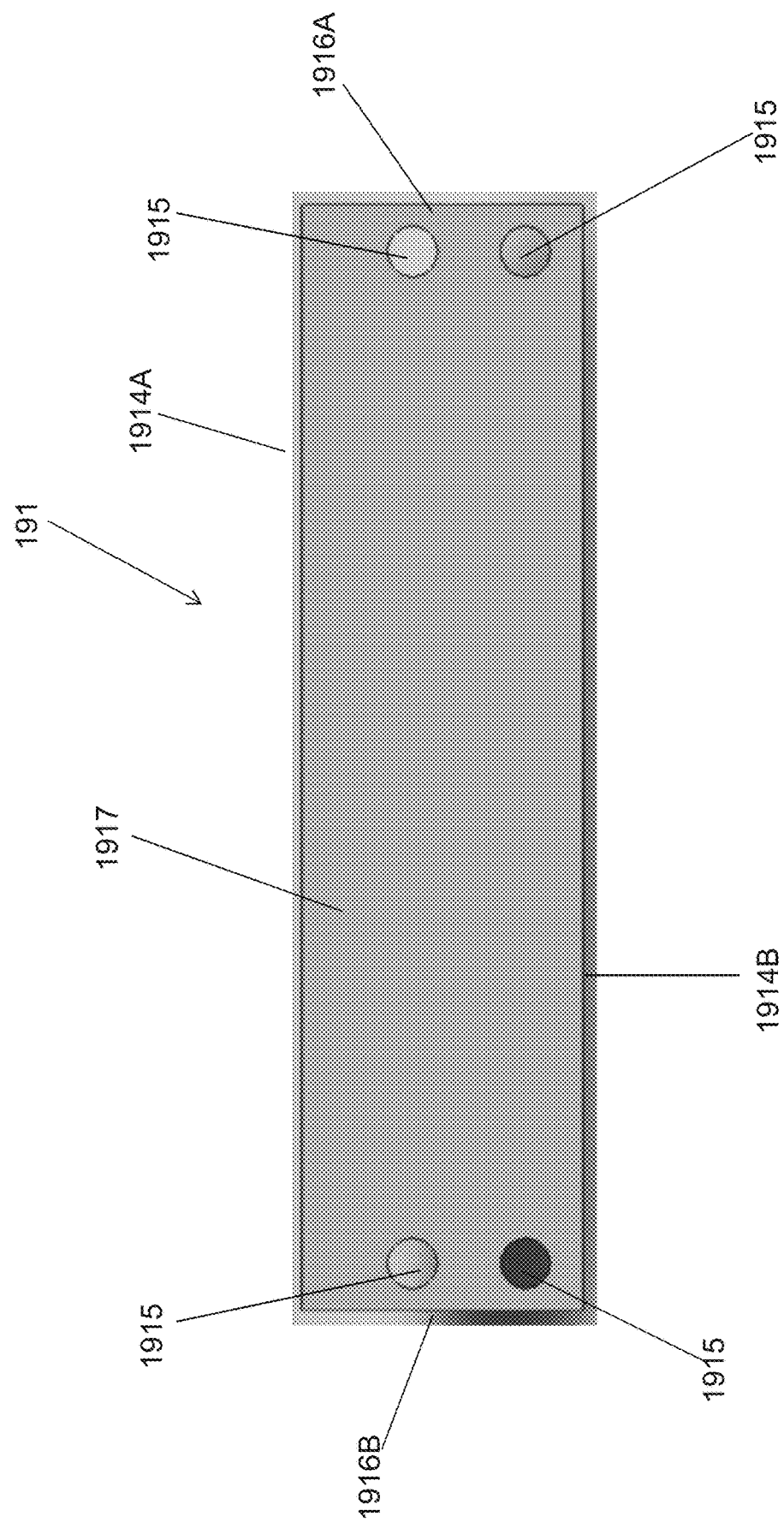
FIG. 32 illustrates a first portion of the ramp member.
Figure 33:
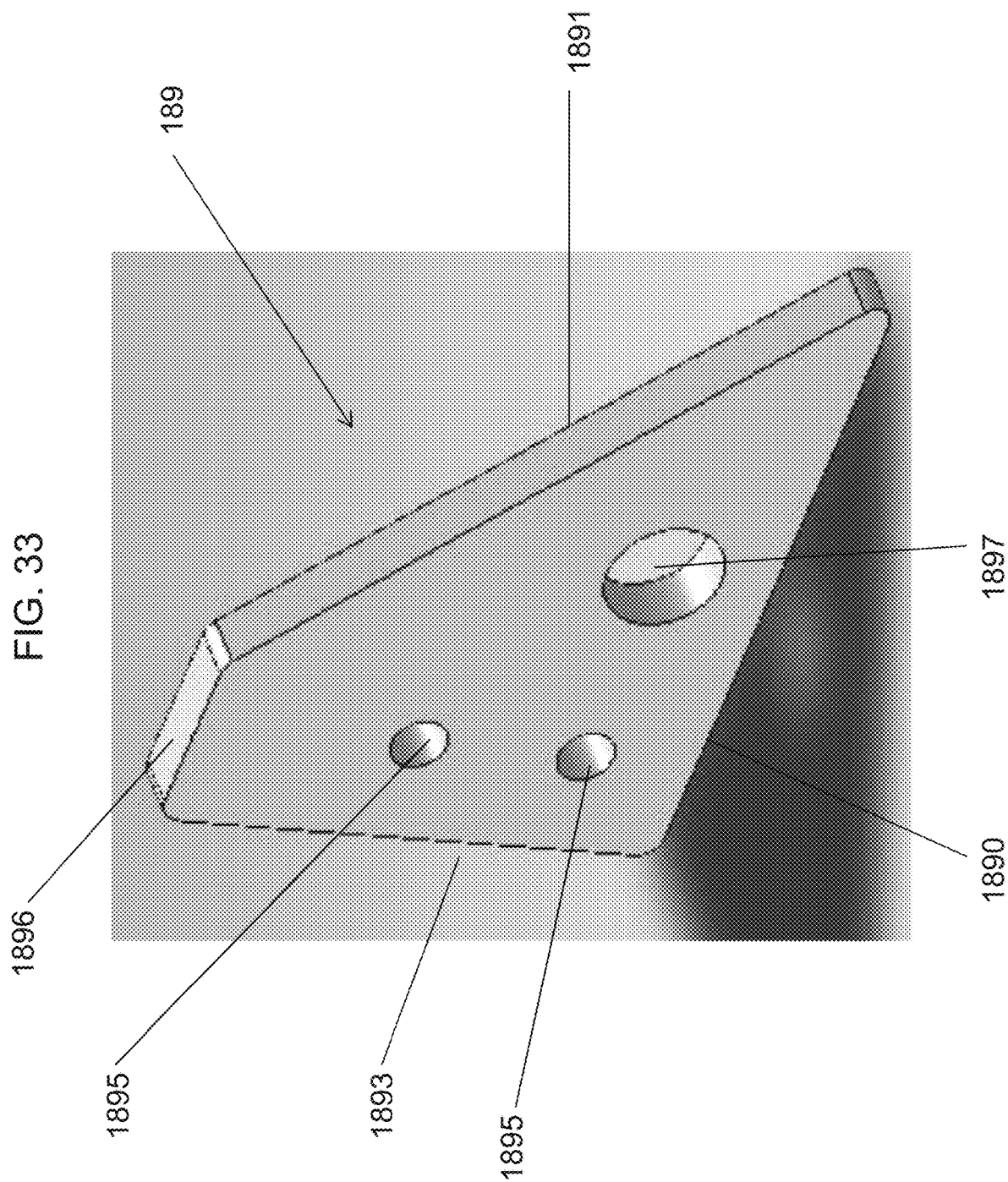
FIG. 33 illustrates the corner brackets.
Figure 34:
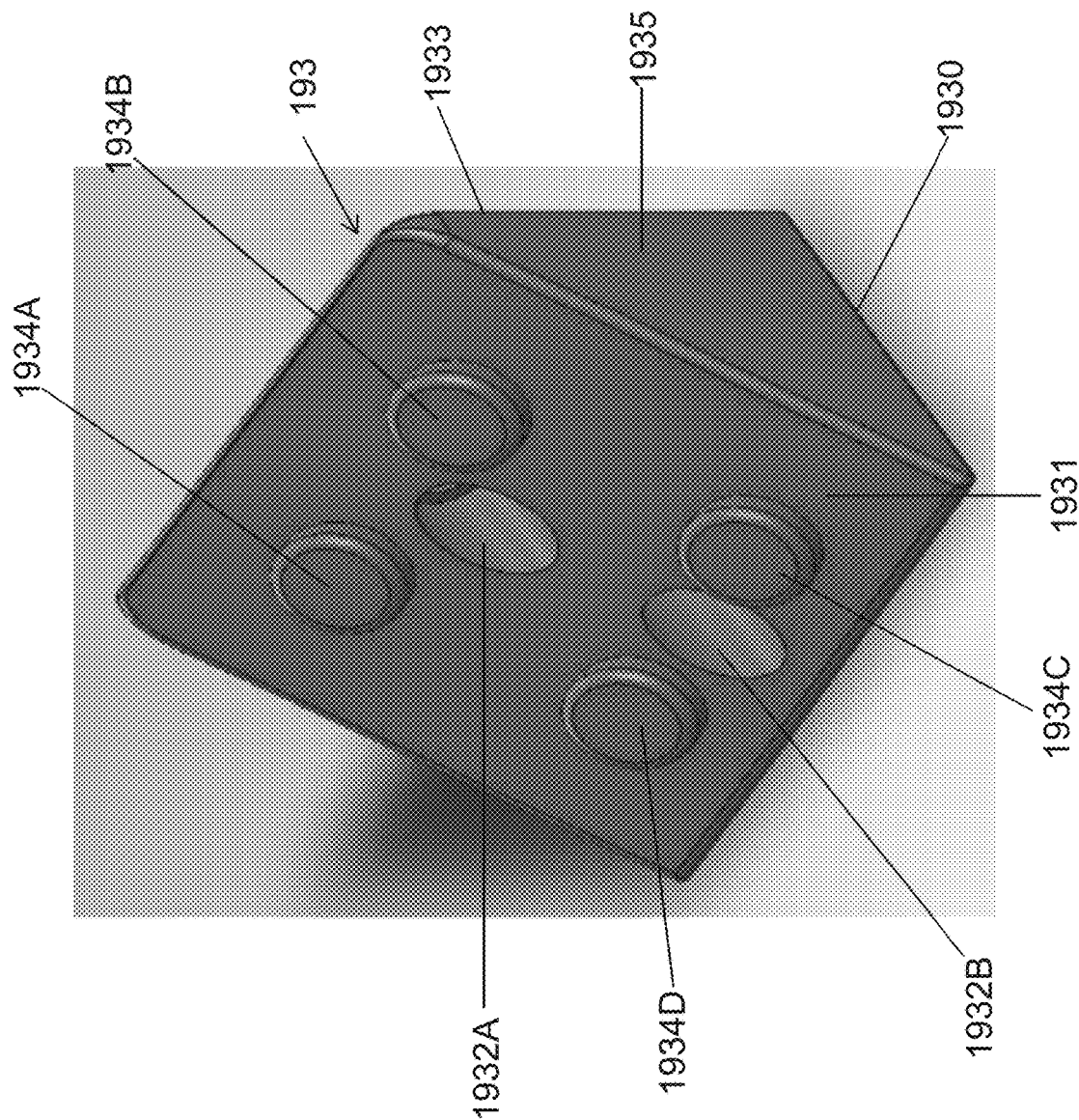
FIG. 34 illustrates a side face of the ramp.

The mat may include a pump corner ramp member 200. For example as shown in FIG. 31, the pump corner ramp member 200 has a front face 2001, a rear face 2002, a first set of opposing edges 2006A-B, and a second set of opposing edges 2004A-B. The pump corner ramp member 200 may be fixedly attached to the center ramp connector 193A-B with the rear face 2002 of the ramp 190A-B being in contact with the center ramp connector 193A-B.

The bottom face of the standing surface 120A-B may have a plurality of ribs 162 attached thereto. For example as shown in FIG. 6, each rib 162 may have a fluid outlet holder 167 connected to a surface. The ribs 162 may be fixedly attached to the bottom face of the standing surface 120A-B. The fluid outlets 160 may be configured to deliver fluid through the standing surface 120A-B. The inner edges of the frame may have a plurality of protrusions configured to accept the edges of the rib members 162. The communication of the rib member 162 and the protrusions on the inner edges of the frame may provide additionally support for the standing surface.

The mat may also include a plurality of flat brackets 189. Each flat bracket 189 may have a pair of side faces 1894A-B that oppose each other. The flat brackets 189 may also include a bottom edge 1890, a front edge 1891, and a rear edge 1893. The bottom edge 1890, the front edge 1891, and the rear edge 1893 of the flat brackets may meet one another to form a triangle. The flat brackets may have a top edge 1896 opposite the bottom edge 1890. The flat bracket may include apertures 1895A-B for receiving screws, bolts or other fasteners. The flat bracket may also include apertures 1897 for receiving a protrusion from a corner bracket.

One of the flat brackets may be configured to be placed in the same corner as the pump 150. Because the pump corner may have different dimensions from the other corners, a pump corner flat bracket 194 may serve the same purpose as the other flat brackets 189. The pump corner flat bracket 194 may have a pair of side faces 1944A-B that oppose each other. The pump corner flat bracket 194 may also include a bottom edge 1940, a front edge 1941, and a curved rear edge 1943. The bottom edge 1940, front edge 1941, and curved rear edge 1943 of the pump corner bracket may meet one another to form a triangular shape. The pump corner flat bracket may include apertures 1945A-B for receiving screws, bolts or other fasteners. The pump corner flat bracket may also include apertures 1947 for receiving protrusions 1165A-B from a corner bracket 116.

The sanitizing mat 100 may include a plurality of ribs 162 that extend from the center column 180. For example as shown in FIG. 6, the ribs 162 may have a top face 1621 and a bottom face 1620. The bottom face 1620 may include an I-beam structure 1626. The ribs 162 may also have a first end 165 that is configured to be attached to an edge of the center column 180. The ribs 162 may have a second end 166 that is configured to be received by an inner edge of the frame. The ribs 162 may also have an oblong aperture 169 configured for having fluid outlet holders 167 slidably engaged to the ribs 162. The ribs 162 may serve at least two purposes. First, the ribs 162 provide additional support for a standing surface that may rest atop the top face 1621 of the rib. The bottom face 1620 of the rib 162 may have a plurality of fluid outlet holders 167 attached thereto. The ribs 162 may be made of a rigid material such as plastic or metal. In some embodiments the ribs 162 do not provide additional support for a standing surface 120A-B. In such embodiments, the ribs 162 may be used exclusively for holding fluid outlets 167.

The center column's second set of opposing edges 184A-B may have a standing surface 120A-B affixed to each edge 184A-B of the center column 180. The edges 184A-B of the center column 180 that are attached to brackets are fixedly attached to each bracket. The edges of the center column 180 may be pivotally attached to one or more brackets. In other embodiments the edges 184A-B may be removably attached to one or more brackets.

The sanitizing mat 100 has a standing surface 120A-B that is attached to at least one bracket. In some embodiments the sanitizing mat 100 may have two standing surfaces. For example as shown in FIGS. 1-3 and 7-9, the standing surface 120A-B may each have a bottom face 1200A-B and a top face 1201A-B. Each standing surface 120A-B may have a rectangular shape with a first set of opposing edges consisting of an outer edge 1202A-B and an inner edge 1204A-B. The standing surfaces also include a second set of opposing edges 1203A-D. The inner edges 1204A-B may have a plurality of apertures 122 configured to be attached to a first end 165 of the ribs and an edge of the center column. The inner edges 1204A-B of each standing surface, first end 165 of the ribs, and an edge 184A-B of the center column 180 may be configured to be attached to one another by a bolt, screw or other fastener. One of skill in the art will appreciate that the inner edges 1204A-B of each standing surface, first end 165 of the ribs, and an inner edge 1204A-B of the center column may be attached to one another without any fastener. The standing surface 120A-B may be one unitary member. The standing surface 120A-B may also be two members, each member attached to an edge of the center column 180.

Figure 8:
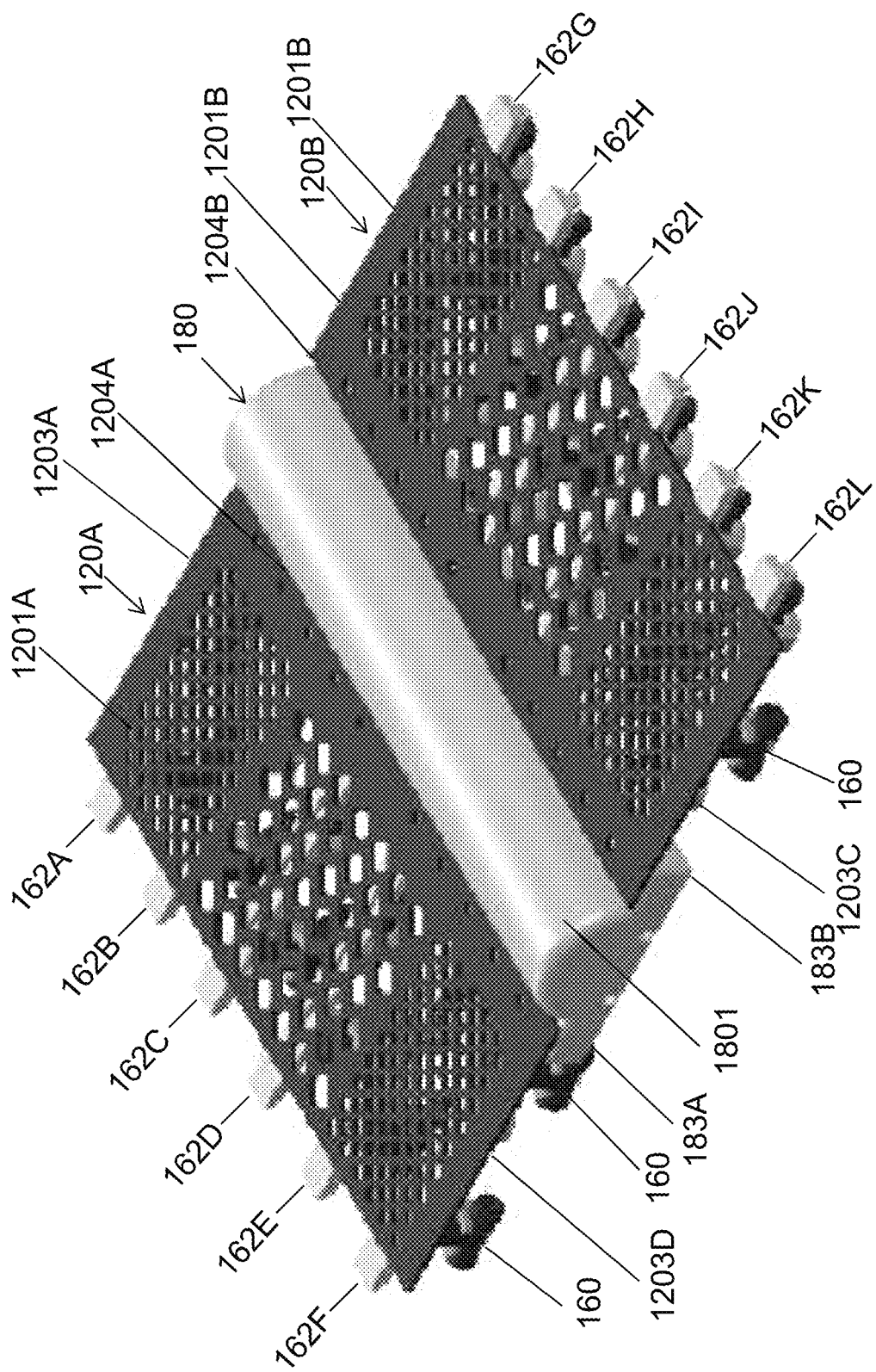
FIG. 8 illustrates a perspective view of the sanitizing floor mat without side housings or ramps.
Figure 10:
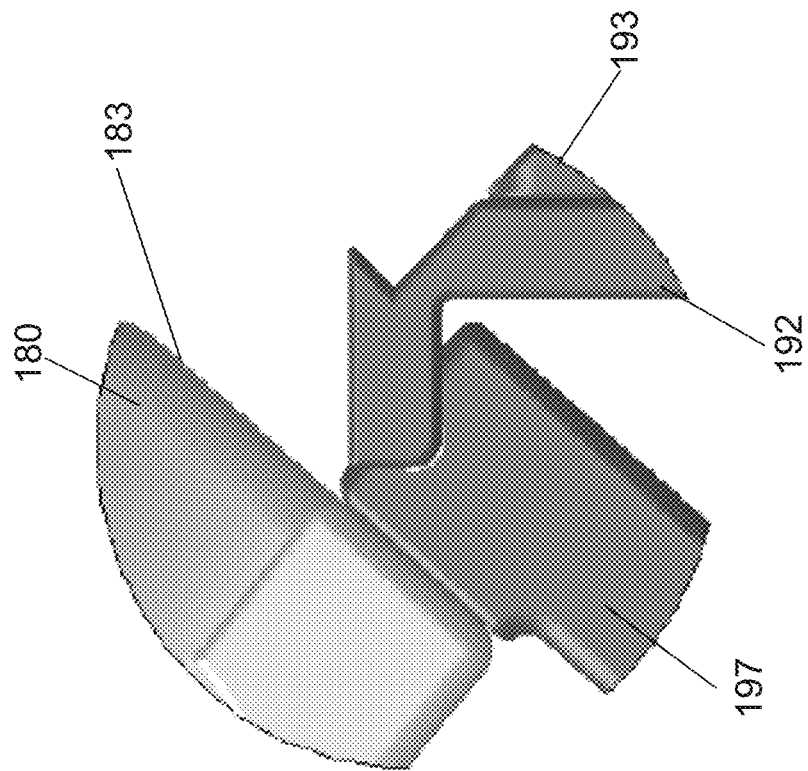
FIG. 10 illustrates the center column and pivot joints of the sanitizing floor mat.
Figure 11:
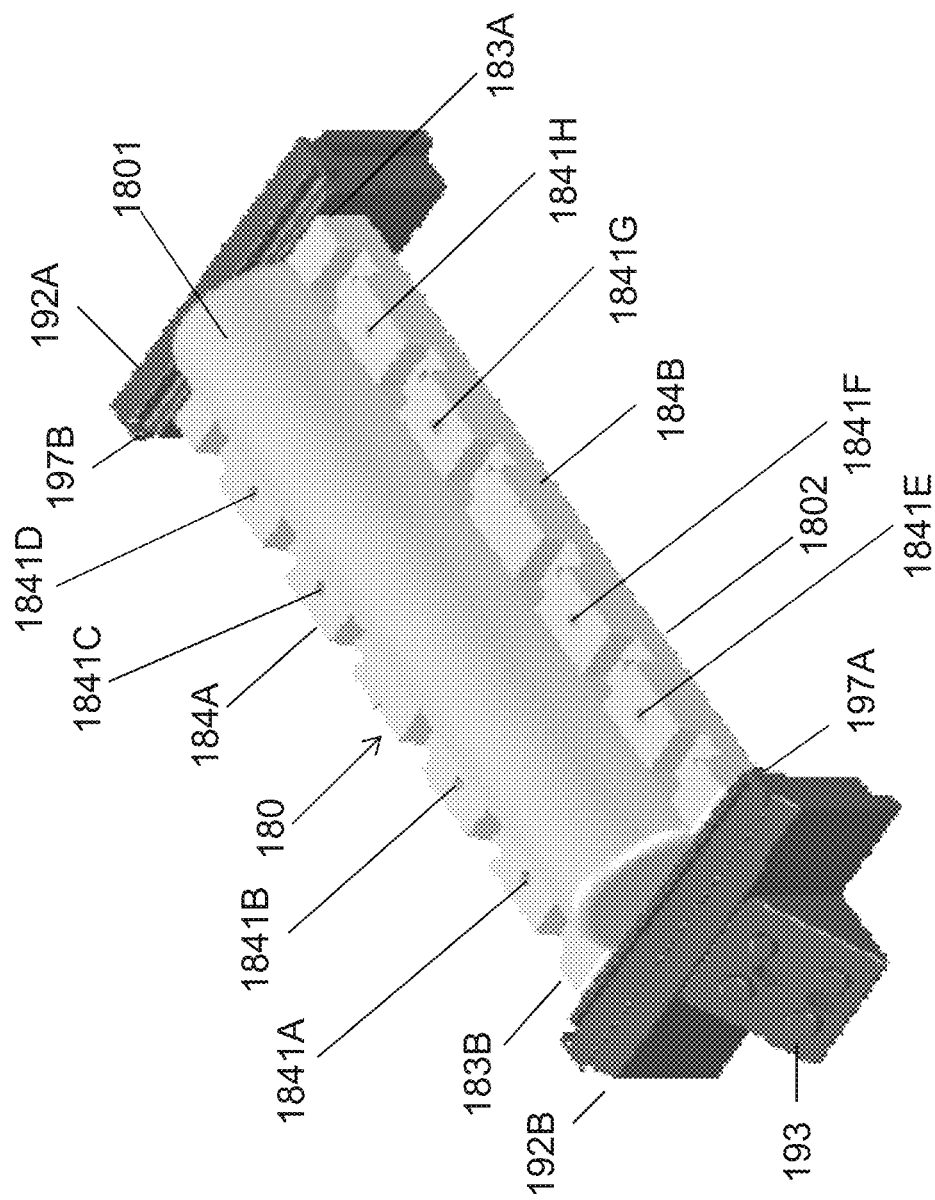
FIG. 11 illustrates the center column and ramp connectors of the sanitizing floor mat.

The standing surface 120A-B may be any surface that allows fluid to pass from the fluid outlets 160 to a user's feet standing on the top face 1201A-B of the standing surface 120A-B. For example as shown in FIGS. 7-9, the standing surface 120A-B may have a plurality of apertures that allow fluid to pass through. The standing surface 120A-B may be a pair of grates 120A-B connected to the center column 180. The apertures of the standing surface 120A-B may be one uniform size or a distribution of sizes.

The standing surface 120A-B may have dimensions that are appropriate for a user's feet to fit inside each standing surface 120A-B. Each standing surface 120A-B should have dimensions that are appropriate for accommodating various sizes of user feet. As a non-limiting example, each standing surface 120A-B may be a 12 inch by 15 inch rectangle. Each standing surface 120A-B may be a 10 inch by 20 inch rectangle. The standing surface 120A-B may be one unitary member that may be a 30 inch by 20 inch rectangle.

Figure 19:
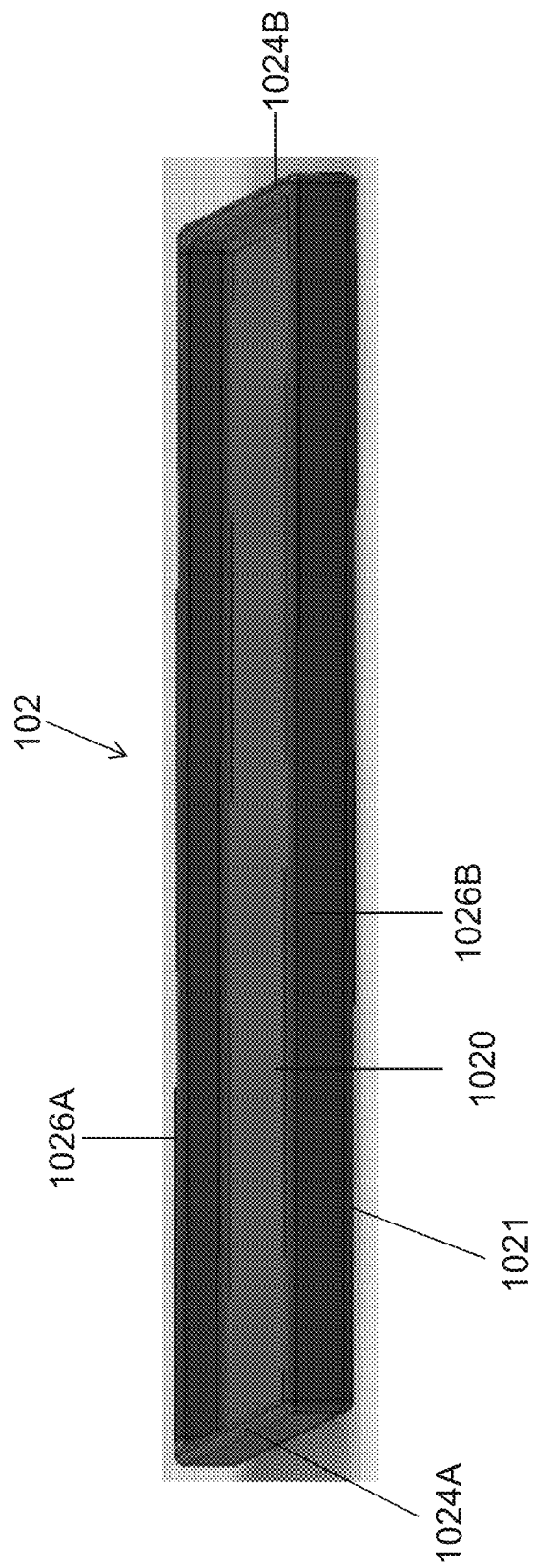
FIG. 19 illustrates the debris tray of the sanitizing mat.
Figure 20:
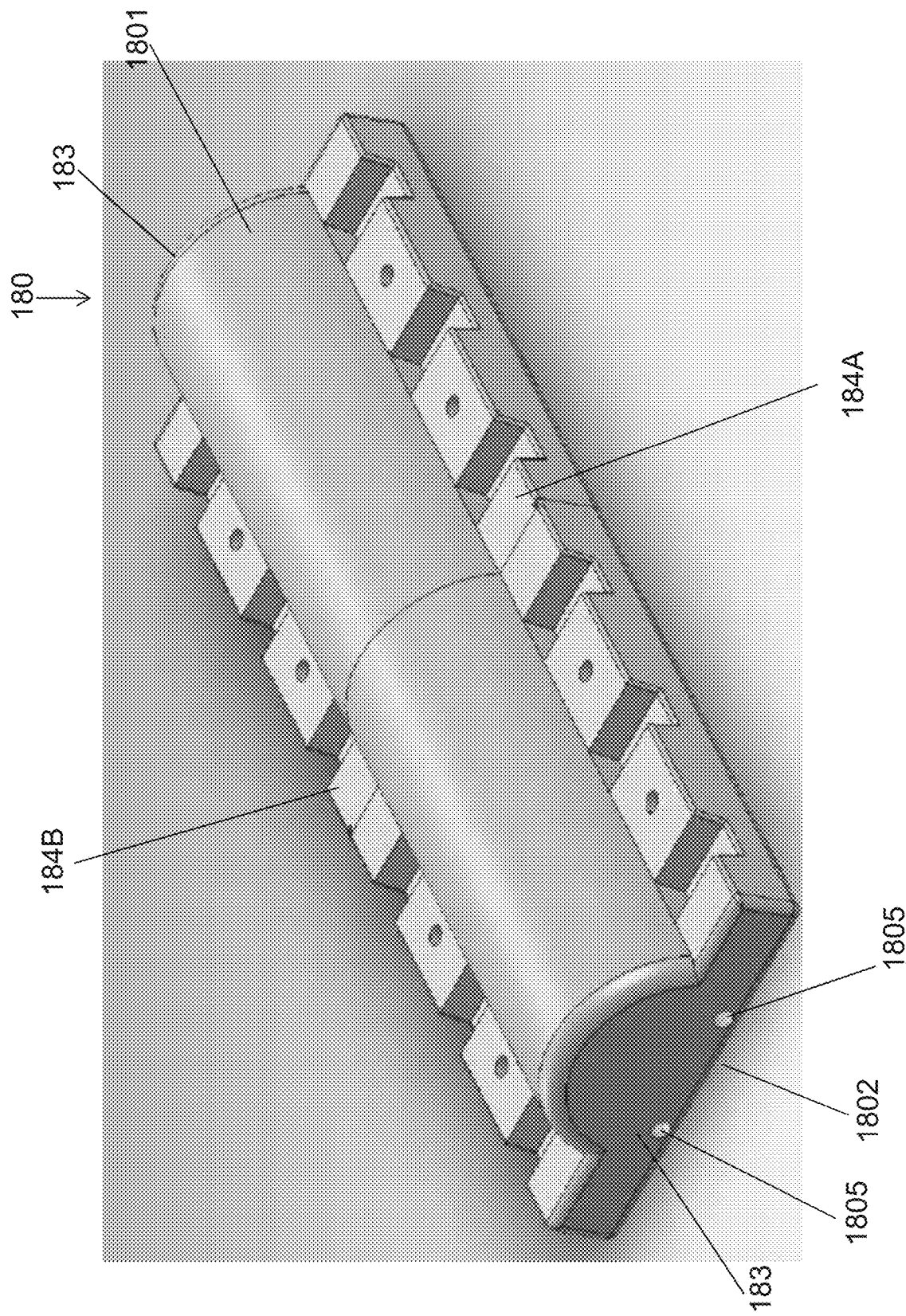
FIG. 20 illustrates a view of the center column of the sanitizing mat.
Figure 21:
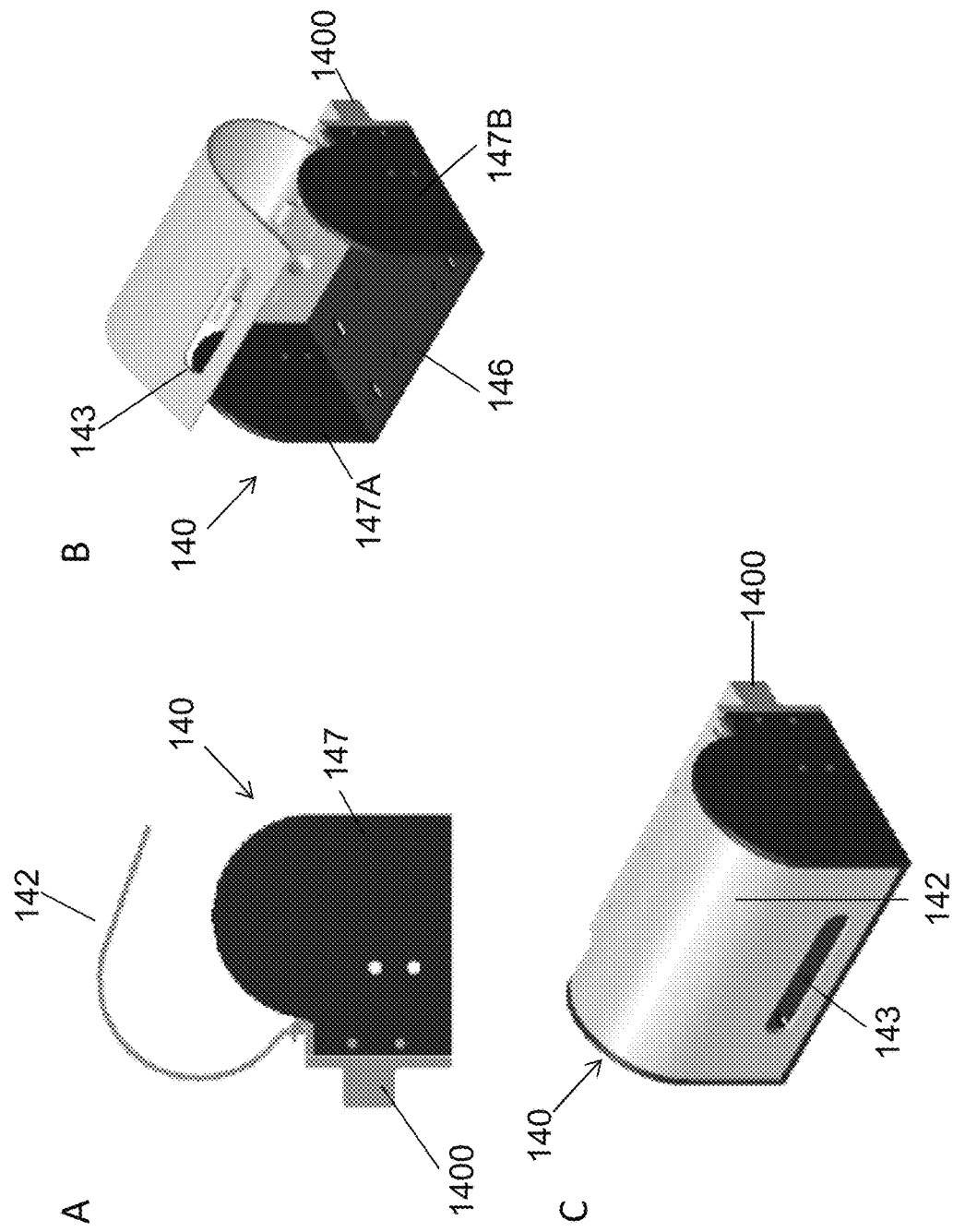
FIG. 21 illustrates a view of the open side housing units of the sanitizing mat.
Figure 22:
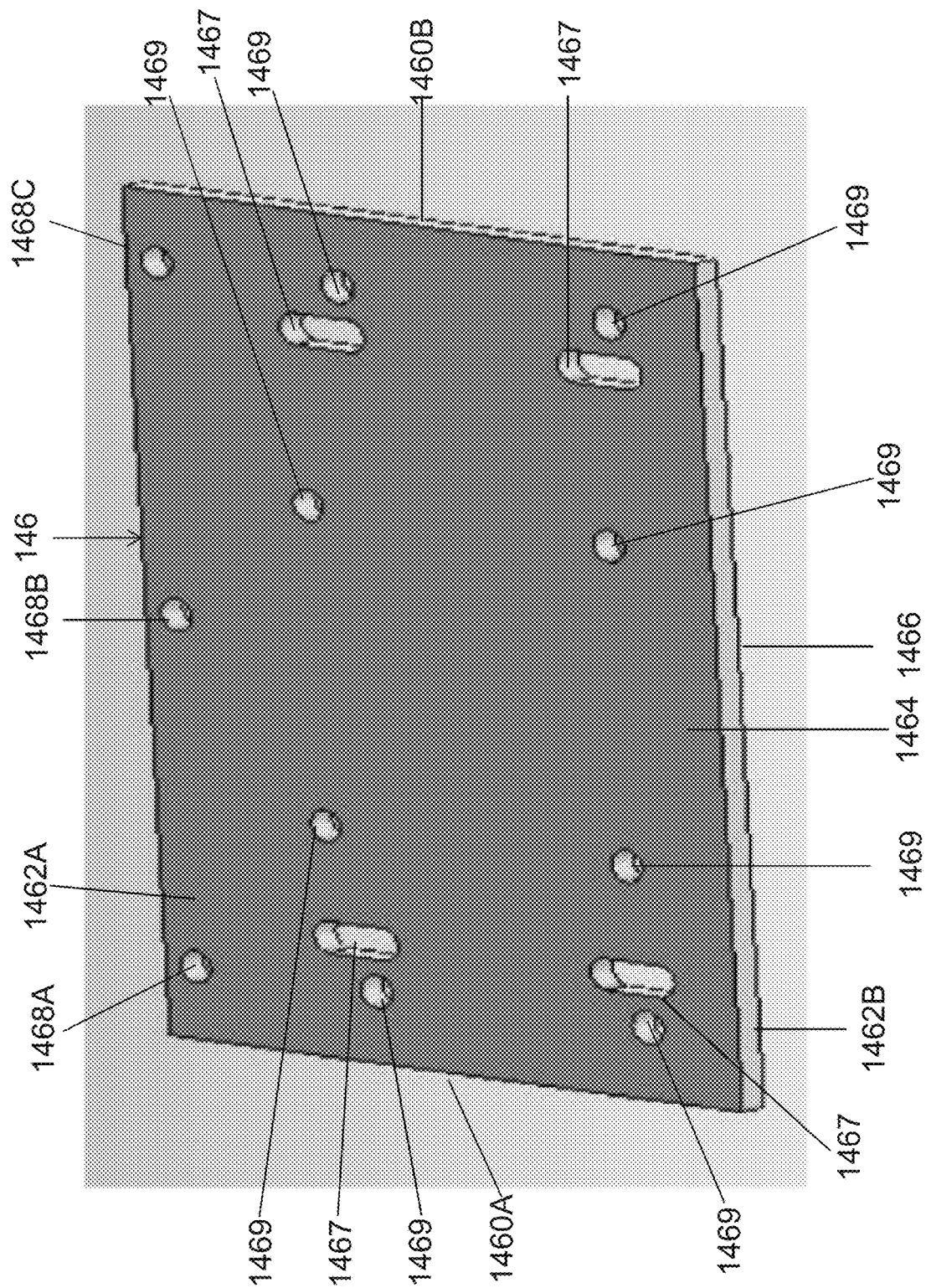
FIG. 22 illustrates the side housing base.
Figure 23:
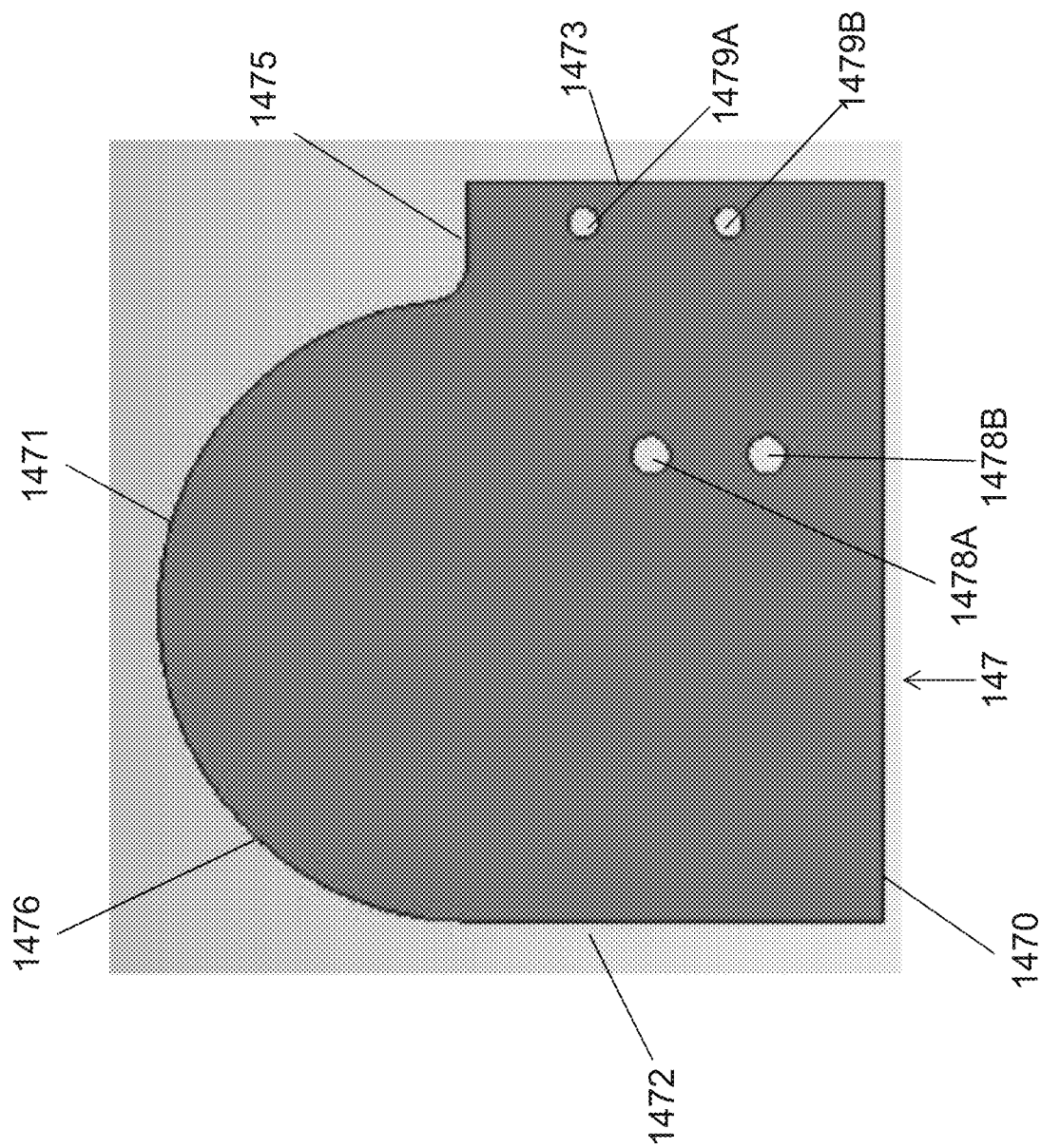
FIG. 23 illustrates a side housing wall.
Figure 24:
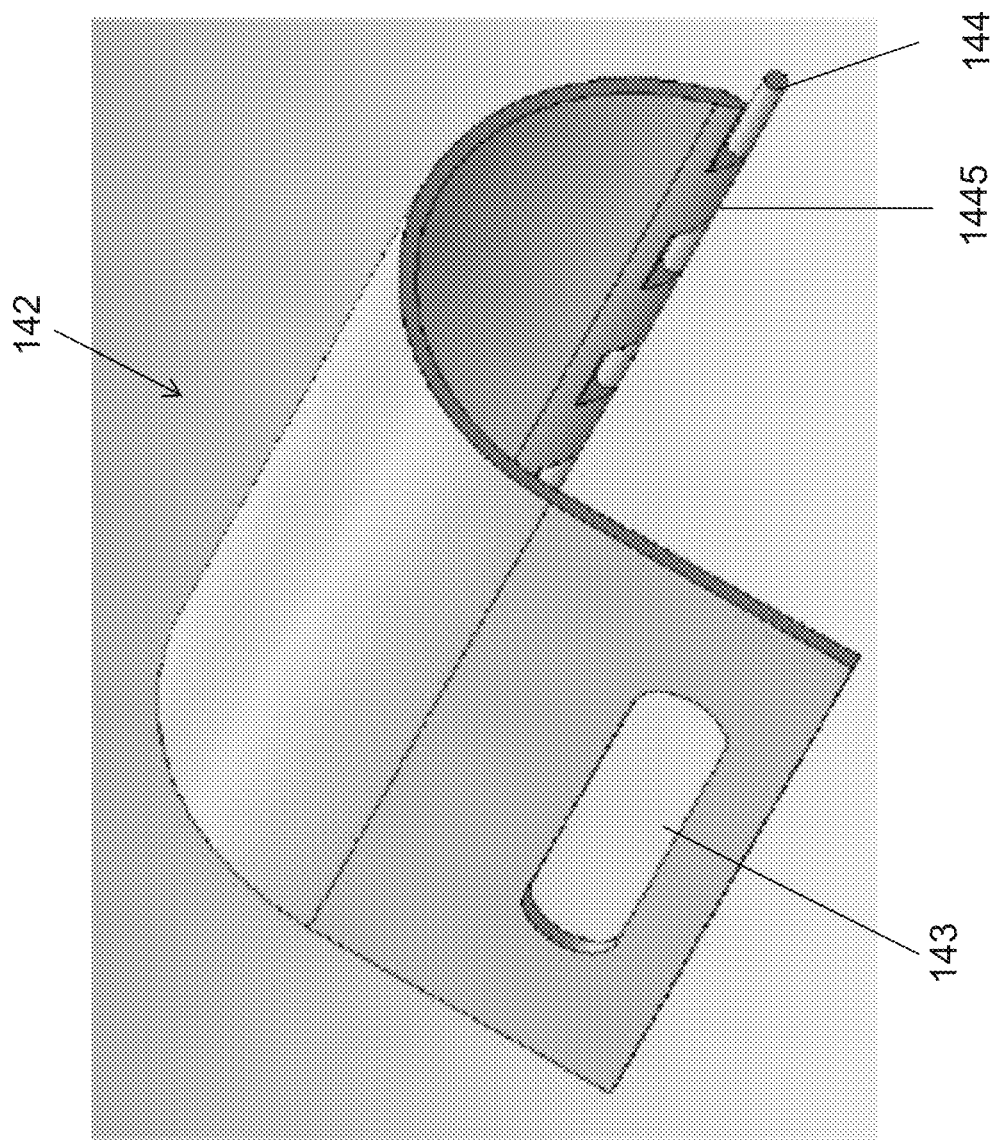
FIG. 24 illustrates a side housing door.
Figure 25:
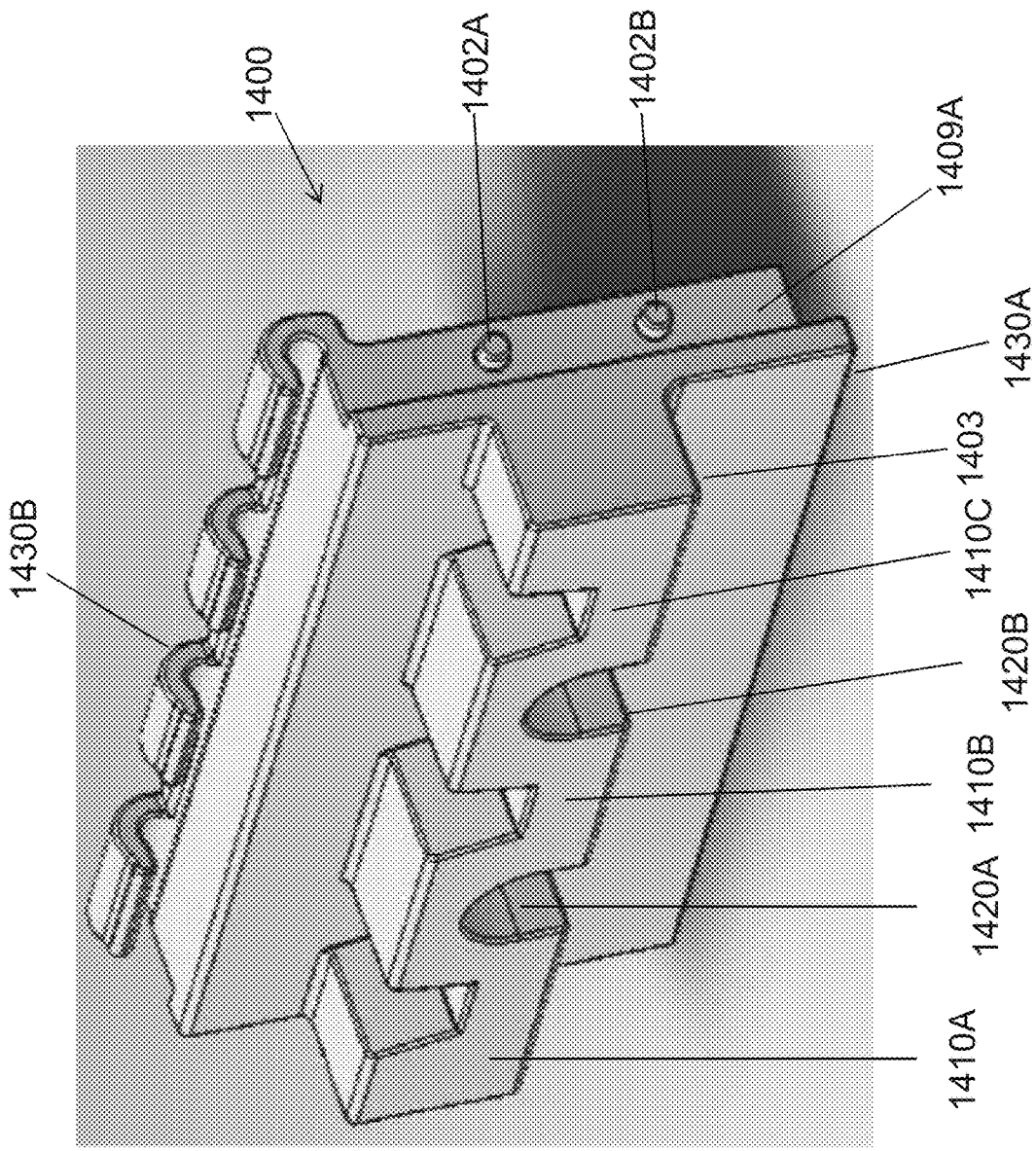
FIG. 25 illustrates a first view of the side housing bracket.

The sanitizing mat 100 may include a removable tray 102 configured to catch debris or liquid. For example as seen in FIG. 19, the rectangular tray 102 has a top face 1020, a bottom face 1021, and two pair of opposing edges. The first set of opposing edges 1024A-B are raised. The second set of opposing edges 1026A-B are also raised. In a closed disposition, the top face 1020 of the tray 102 is opposite the bottom face 1200A-B of the standing surface 120A-B. The tray 102 may be a rectangular member that has dimensions that allow the tray 102 to be received by the frame 110. The tray 102 may be made of a disposable material allowing the user to dispose of the tray 102 once it is filled with debris and fluid. In other embodiments, the tray 102 may be made of a plastic, a metal, or a rubber or any combination thereof. One of skill in the art will appreciate that the tray 102 may be made of any material that is appropriate for catching debris and fluid. One of skill in the art will also appreciate that the tray may have a circular, square, or any other shape known in the art.

The sensor may be configured for detecting the presence of a user. In response to the presence of a user, the sensor may send a signal to the electrical circuit 154, which activates the fluid delivery system. Activation of the fluid delivery system causes fluid to be pumped from the reservoir 152 to the fluid outlets 160. The sensor may be a pressure sensor, a light sensor, a proximity sensor, or a thermal sensor. One of skill in the art will appreciate that any sensor known in the art may be used. One of skill in the art will also appreciate that more than one sensor may be used. One of skill will also appreciate that the sensor may be attached to any surface of the sanitizing mat 100. In some embodiments the sensor may be placed at a location that is not on a surface of the sanitizing mat, but where the sensor can still detect the presence of a user. As a non-limiting example, the sensor may be placed at an entryway or above the sanitizing floor mat 100. In some embodiments a user or a third party may manually activate the sanitizing mat 100 by using a remote control or other method for sending a signal to the electrical circuit, which activates the fluid delivery system.

Figure 15:
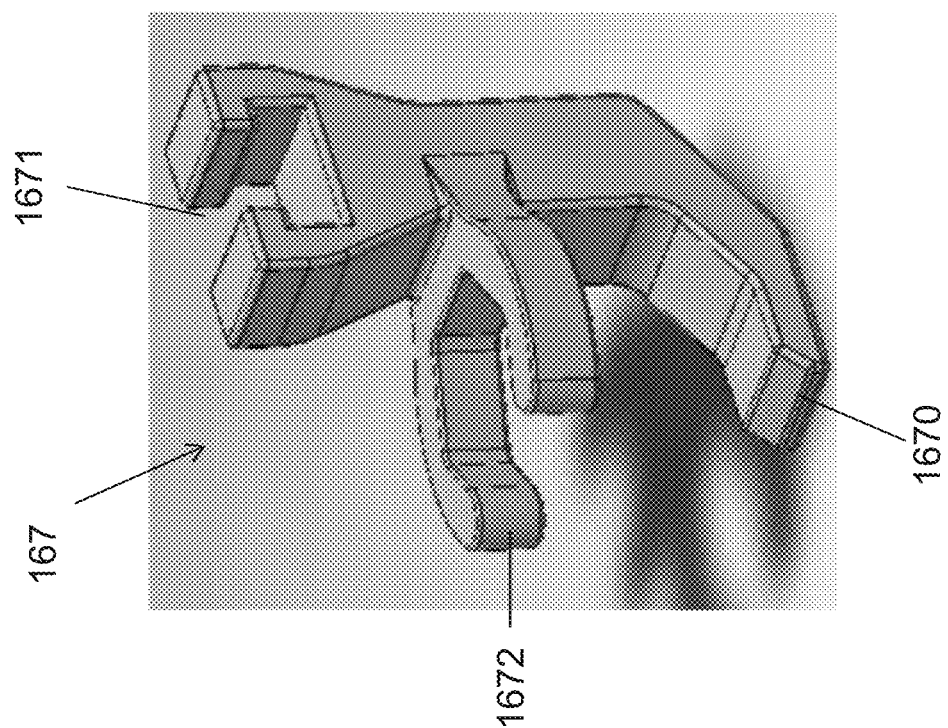
FIG. 15 illustrates a view of a fluid outlet holder.
Figure 16:
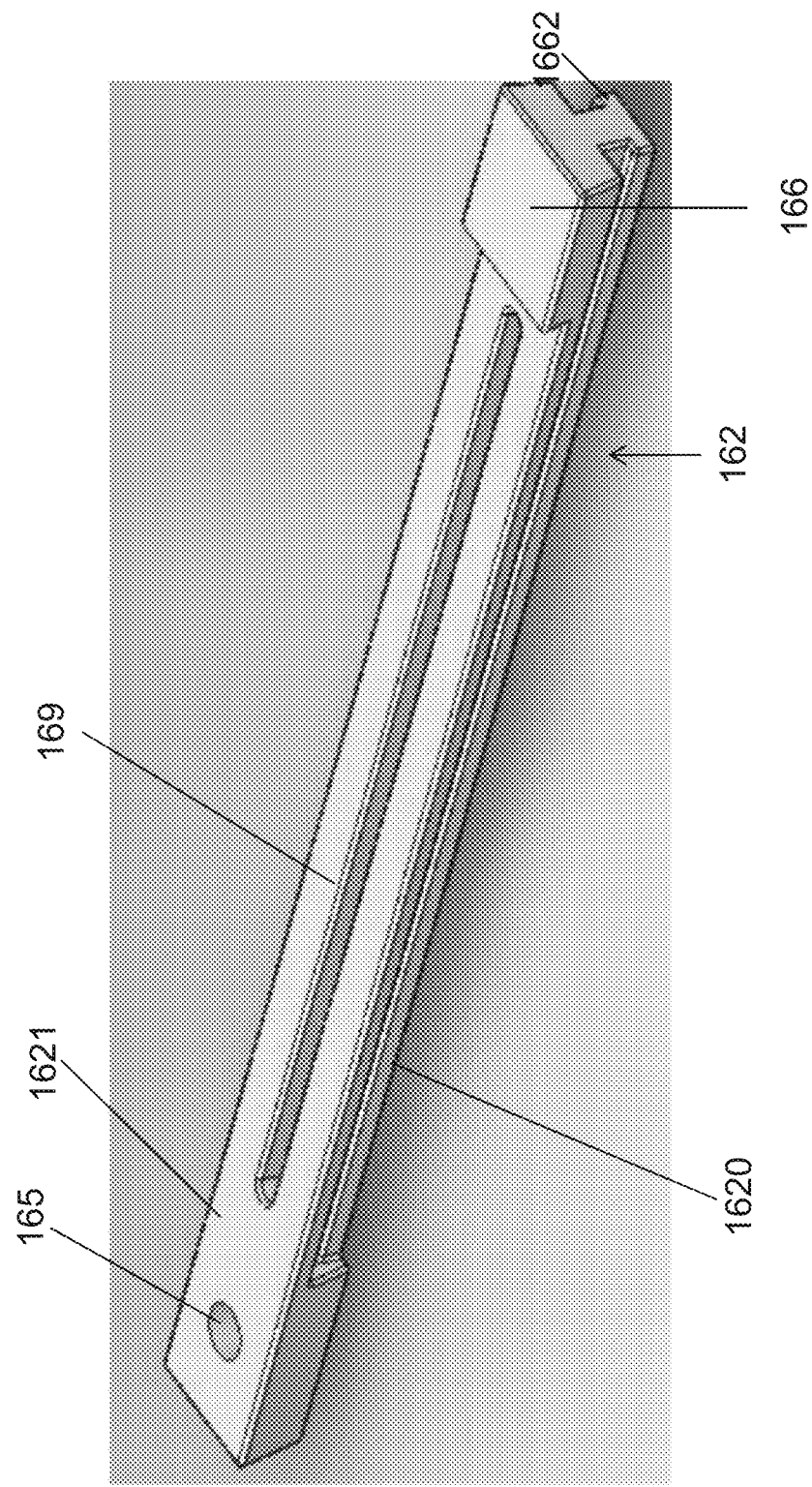
FIG. 16 illustrates a view of a rib of the sanitizing mat.
Figure 17:
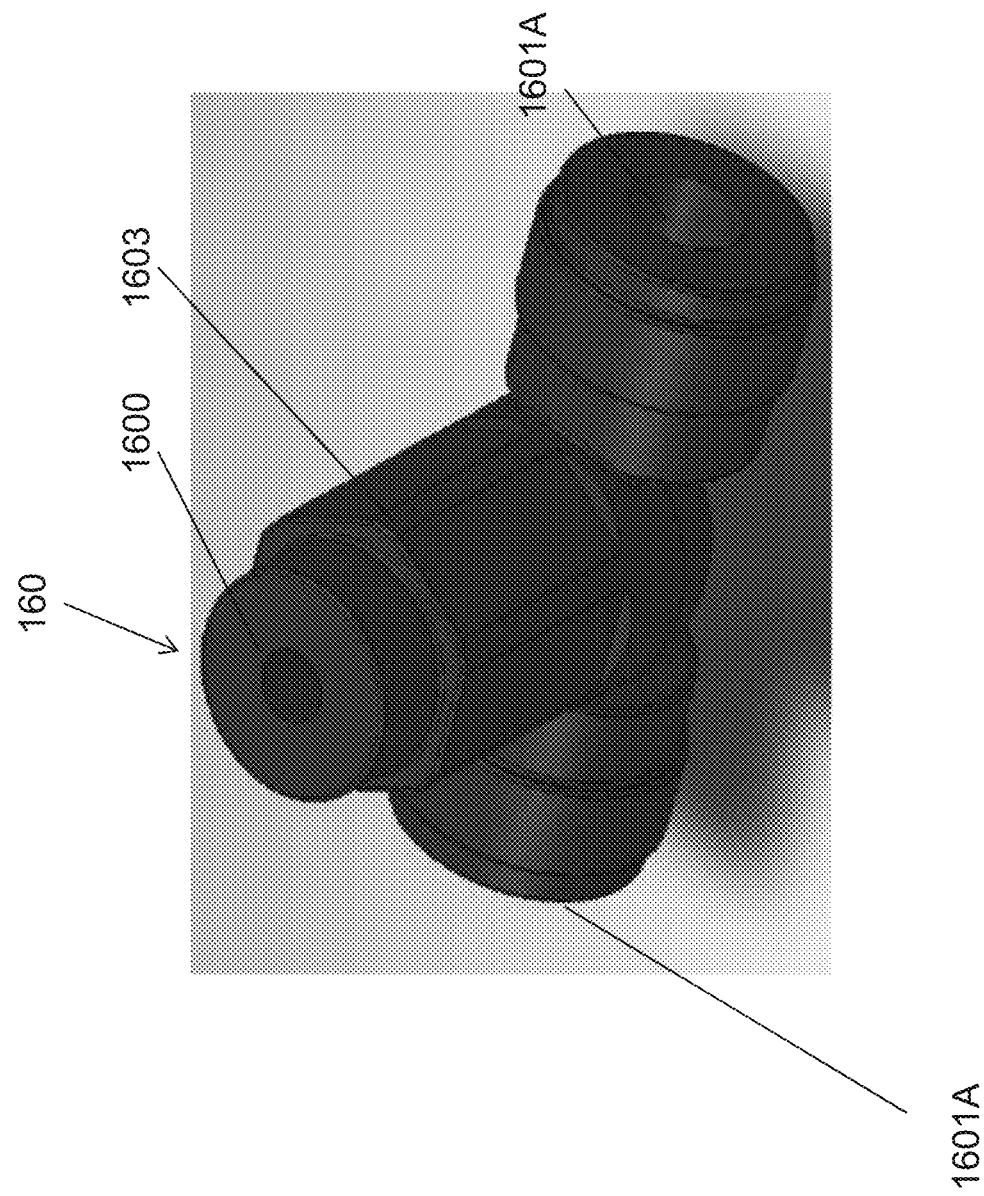
FIG. 17 illustrates a view of a fluid outlet.

The sanitizing mat 100 has a plurality of fluid outlets 160. The fluid outlets 160 may be nozzles for delivering a stream of fluid. For example as shown in FIG. 6, the fluid outlets 160 may be held opposite the bottom face of the standing surface 120 by the fluid outlet holders 167. The fluid outlets 160 may be diffusers for delivering a mist of fluid. The sanitizing mat 100 may have a combination of nozzles and diffusers. For example as shown in FIGS. 15-17, the fluid outlet holder may have an upper portion 1671 that is configured to slide onto the I-beam portion 1626 of a rib member 162. The fluid outlet holder 167 may also have a holder portion 1672 that is configured to receive the main body portion 1603 of the fluid outlet 160. The fluid outlet may have one or more apertures 1600 for dispensing fluid. The fluid outlet 160 may also have one or more inlets 1601A for accepting fluid from the pump. One of skill in the art will appreciate that the fluid outlets 160 may be any nozzle, diffuser, or other apparatus for delivering fluid known in the art.

The reservoir 152 is configured to hold a fluid. The fluid may be a sanitizing fluid. Accordingly, the reservoir 152 is made of a material that can safely store the sanitizing fluid held within the reservoir. The reservoir 152 may be outside of the sanitizing mat 100. The reservoir 152 is in fluid communication with a pump 150 that is configured to pump fluid from the reservoir 152 to the fluid outlets 160. The pump 150 may be any type of pump known in the art, including centrifugal or displacement type pumps. One of skill in the art will appreciate that the pump 150 may be powered by battery, AC power, or any other power source known in the art.

The sanitizing mat 100 may have a sanitization indicator. The sanitization indicator is configured to indicate when sanitization is complete. The sanitization indicator may be located on a top surface of the sanitizing mat 100. One of skill in the art will appreciate that the sanitization indicator may be located anywhere where the user can receive notice that sanitization is complete. The sanitization indicator may be in communication with the electrical circuit 154. The sanitization indicator may be configured to illuminate once a sanitization event has completed. In other embodiments the sanitization indicator is configured to make an audible sound once a sanitization event has completed. One of skill in the art will appreciate that the sanitization indicator may use any means known in the art to notify the user that the sanitization process is complete.

The sanitizing mat 100 may be used for sanitizing a bottom surface of a user's feet. The sanitizing mat 100 may be used for sanitizing the bottom surface of a user's shoes. One of skill in the art will appreciate that the sanitizing mat 100 may be used for sanitizing any surface that contacts the mat 100.

The sanitizing mat 100 delivers a sanitizing fluid to the feet of a user. The sanitizing fluid may include water. The sanitizing fluid may also include one or more fast drying antiseptics such as alcohols. One of skill in the art will appreciate that the alcohol does not have to be fast drying. The sanitizing fluid may include an aldehyde, a phenolic compound, a quaternary ammonium compound, a silver compound, a thymol-based compound, or sodium hypochlorite. One of skill in the art will appreciate that the sanitizing fluid may include any antimicrobial composition known in the art.

Method:

The sanitizing mat may be used to sanitize the feet of a user. The sanitizing mat may be used by first placing a user's feet on the standing surface of the mat. The presence of a user is detected by a sensor. The sensor then sends a signal to the electrical circuit, which causes the circuit to activate the fluid delivery system causing fluid to be pumped from the reservoir to the fluid outlets. While fluid is being delivered to the user's feet, the user stands on the standing surface until the sanitization indicator provides a signal that sanitization is complete. Once the sanitization process is complete, the user may step off of the sanitizing mat. The user may step onto a towel or other surface configured to dry the users feet. One of skill in the art will appreciate that the drying surface may utilize any method of drying, including but not limited to suction, blowing, heat, or absorption. The user may remove their feet without receiving a signal from the sanitization indicator.

It may be desirous to decontaminate a user's feet upon leaving a facility such as a food processing facilities. Because the sanitizing mat may have a ramp on each side, a user may walk onto the sanitizing mat from either side. Accordingly, a user leaving a facility, may step onto the sanitizing mat and sanitize their feet according to the same method used for sanitizing feet upon entering a facility.

Example

It is often desirous to sanitize the feet or shoes of a person entering an aseptic environment. For example, an intensive care unit of a hospital may require that doctors, patients, or visitors sanitize their feet prior to entering the room. The sanitizing floor mat may be used for sanitizing the feet of entrants into an aseptic environment.

By way of non-limiting example, the reservoir of the sanitizing floor mat was loaded with a sanitizing fluid. The sanitizing floor mat was placed at the entrance of an intensive care unit. As a person entered the room, the person stepped onto the grate of the apparatus. The weight of the person caused a pressure sensor to send a signal to the apparatus processor. The processer then sent a signal to the reservoir-pump system causing the reservoir-pump system to discharge a predetermined amount of sanitizing fluid through the fluid outlets. The sanitizing fluid exited the fluid outlets in a combination of mist and spray. The sanitizing mist and spray then contacted the persons feet, killing or incapacitating a statistically significant amount of microbes. After standing on the grate for a predetermined time, the sanitizing floor mat provided a signal that the person's feet had been sanitized. The person then entered the aseptic room with their feet free of debris and microbes.

What is claimed is:

1. A sanitizing mat, designed to be placed on a surface and spray sanitizing fluid when activated by a user, the sanitizing mat comprises:
   a fluid delivery system, wherein the fluid delivery system includes a plurality of reservoirs in fluid communication with at least one pump, the at least one pump and the plurality of reservoirs are in fluid communication with one or more fluid outlets;
   a sensor configured to detect the presence of a user and activate the fluid delivery system;
   a rectangular frame member having two sets of opposed edges;
   an elevated standing surface above the rectangular frame, wherein the elevated standing surface is a pair of rectangular or square grates;
   a housing configured to hold the at least one pump and the plurality of reservoirs, wherein the housing has a door pivotally attached;
   a first bracket affixed to the housing and the rectangular frame, and a second bracket, wherein the first and second brackets oppose one another, and wherein each of the first and second brackets has a ramp affixed thereto; and
   a center column rotatably affixed to the first and second brackets, the center column having a first pair of opposing edges and a second set of opposing edges, wherein the first pair of opposing edges is affixed to the first and second brackets, and the second set of opposing edges attached to a first and a second grate.

2. The sanitizing mat of claim 1, wherein the sensor is configured to detect the presence of the user so that the at least one pump is activated causing fluid to be expelled from the plurality of reservoirs to the one or more fluid outlets.

3. The sanitizing mat of claim 2, further comprising an electrical circuit in communication with the sensor and the fluid delivery system, whereby the electrical circuit controls the fluid delivery system.

4. The sanitizing mat of claim 1, wherein the plurality of reservoirs is configured to store an antimicrobial solution.

5. The sanitizing mat of claim 1, further comprising at least one indicator to indicate the completion of a sanitizing process.

6. The sanitizing mat of claim 1, wherein pair of the rectangular or square grates is configured to allow a fluid expelled from the fluid delivery system to contact the feet of a user standing on the pair of rectangular or square grates.

7. The sanitizing mat of claim 1, wherein the one or more fluid outlets are chosen from a group that includes but is not limited to diffusers configured to discharge a mist and nozzles configured to discharge a stream of fluid.

8. The sanitizing mat of claim 1, further comprising a removable tray under the elevated standing surface, wherein the removable tray is configured to catch debris that is removed from the foot of a user.

9. The sanitizing mat of claim 1, wherein the sensor is chosen from a group consisting of pressure sensors, light sensors, proximity sensors, or thermal sensors.

10. The sanitizing mat of claim 1, wherein the one or more fluid outlets are located between the elevated standing surface and the rectangular frame.

11. The sanitizing mat of claim 1, wherein the elevated standing surface is pivotally attached to the rectangular frame.

12. A sanitizing mat for sanitization of shoes and other surfaces in contact with a floor, the sanitizing mat comprising:
   a rectangular frame, the rectangular frame having a first edge opposite a second edge, a third edge opposite a fourth edge, and a top surface opposite a bottom surface, wherein the first and second edge are parallel to one another, the third and fourth edge are parallel to one another, and the first and third edges are perpendicular to one another;
   an elevated standing surface above the rectangular frame;
   at least one reservoir in fluid connection with at least one pump, the at least one pump is in fluid communication with a plurality of fluid outlets;
   at least one grate, wherein the at least one grate is pivotally attached to the rectangular frame and the plurality of fluid outlets are between the at least one grate and the rectangular frame;
   at least one sensor configured to detect a user's presence;
   at least one sanitization indicator; and
   at least one side housing configured to hold the at least one pump and the at least one reservoir.

13. The sanitizing mat of claim 12, wherein the at least one sanitization indicator is light, sound, or a combination thereof.

14. The sanitizing mat of claim 12, wherein a plurality of brackets are connected to the at least one grate and the plurality of fluid outlets are attached to the plurality of brackets.

15. The sanitizing mat of claim 12, wherein the plurality of fluid outlets are nozzles and diffusers.

16. A sanitizing mat for sanitization of shoes or other surfaces in contact with a floor, the sanitizing mat comprising:
   a frame that is a rectangular member having two sets of opposing edges;
   a reservoir, the reservoir configured to store a sanitizing fluid;
   a plurality of fluid outlets, wherein the plurality of fluid outlets are diffusers and nozzles;

a pump, the pump configured to pump fluid from the reservoir to the plurality of fluid outlets;

an electrical circuit;

a first bracket affixed to the frame, and a second bracket, wherein the first and second brackets oppose one another, and wherein each first and second bracket has a ramp affixed thereto;

a center column rotatably affixed to the first and second brackets, the center column having a first face opposite a second face, a first pair of opposing edges and a second set of opposing edges, wherein the first pair of opposing edges are affixed to the first and second brackets and the second set of opposing edges attached to a first and a second grate;

the first and the second grate are configured to support the feet of a user standing on the first and second grates, each grate having a bottom face and a top face, wherein the first and second grates have a plurality of apertures that allow fluid to pass through the first and second grates, wherein the plurality of fluid outlets are connected to the bottom faces of the first and second grates, wherein the first and second grates form an elevated standing surface above the frame;

a sensor for detecting the presence of a user, wherein the sensor is configured to detect the presence of the user so that when the user is detected the pump is activated causing fluid to be expelled from the reservoir to the plurality of fluid outlets;

a removable tray configured to catch debris or liquid, the removable tray located opposite the bottom face of the first and second grates;

a first side housing member and a second side housing member affixed to the first and second brackets, each side housing further comprising a first and a second compartment, each compartment having a side door pivotally attached, each compartment configured to receive the pump, the reservoir, or the electrical circuit;

wherein the pump, the reservoir, and the plurality of fluid outlets are in fluid communication with another; and a sanitization indicator, wherein the sanitization indicator is configured to illuminate once a sanitization event has completed.

17. A method of sanitizing shoes or other surfaces that contact a floor using the sanitizing mat of claim 16, the method comprising;

placing a user's feet on the elevated standing surface;

keeping the user's feet on the elevated standing surface while a fluid contacts the user's feet;

waiting for an indication that the user's feet have been sanitized; and removing the user's feet from the sanitizing mat.

* * * * *

UNITED STATES PATENT AND TRADEMARK OFFICE
CERTIFICATE OF CORRECTION

| | |
|---|---|
| PATENT NO. | : 10,894,108 B2 |
| APPLICATION NO. | : 15/340829 |
| DATED | : January 19, 2021 |
| INVENTOR(S) | : Douglas Jackson |

Page 1 of 1

It is certified that error appears in the above-identified patent and that said Letters Patent is hereby corrected as shown below:

In the Claims

- In Claim 6, Column 14, Line 6, insert --the-- after 'wherein'.

- In Claim 6, Column 14, Line 6, delete "the" at the end of Line 6 following the second occurrence of 'of'.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*